(12) United States Patent
Camire et al.

(10) Patent No.: US 10,239,933 B2
(45) Date of Patent: Mar. 26, 2019

(54) COMPOSITIONS AND METHODS FOR MODULATING THROMBIN GENERATION

(71) Applicant: The Children's Hospital of Philadelphia, Philadelphia, PA (US)

(72) Inventors: Rodney M. Camire, Sicklerville, NJ (US); Matthew W. Bunce, Havertown, PA (US); Mettine H. A. Bos, Amsterdam (NL)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days.

(21) Appl. No.: 15/131,385

(22) Filed: Apr. 18, 2016

(65) Prior Publication Data
US 2016/0222085 A1    Aug. 4, 2016

Related U.S. Application Data

(60) Division of application No. 14/250,840, filed on Apr. 11, 2014, now Pat. No. 9,321,826, which is a continuation-in-part of application No. PCT/US2012/060232, filed on Oct. 15, 2012.

(60) Provisional application No. 61/546,752, filed on Oct. 13, 2011.

(51) Int. Cl.
| | |
|---|---|
| *C07K 14/745* | (2006.01) |
| *A61K 38/36* | (2006.01) |
| *A61K 45/06* | (2006.01) |
| *A61K 38/00* | (2006.01) |

(52) U.S. Cl.
CPC .......... *C07K 14/745* (2013.01); *A61K 38/36* (2013.01); *A61K 45/06* (2013.01); *A61K 38/00* (2013.01); *C07K 2319/35* (2013.01)

(58) Field of Classification Search
CPC ............................. C07K 14/745; A61K 38/36
See application file for complete search history.

(56) References Cited

U.S. PATENT DOCUMENTS

| | | | | |
|---|---|---|---|---|
| 5,563,123 A | * | 10/1996 | Innis | ................ C07K 14/8114 |
| | | | | 514/14.9 |
| 5,696,088 A | | 12/1997 | Innis | |
| 6,900,016 B1 | * | 5/2005 | Venter | .................... C07H 21/04 |
| | | | | 435/320.1 |
| 7,125,846 B2 | | 10/2006 | Rojkjaer | |
| 2002/0173465 A1 | | 11/2002 | Hembrough et al. | |
| 2009/0215046 A1 | | 8/2009 | Sorek et al. | |
| 2009/0318344 A1 | | 12/2009 | Camire et al. | |

FOREIGN PATENT DOCUMENTS

WO    2008/059041    5/2008

OTHER PUBLICATIONS

Walsh, G., "Post-translational Modifications of Protein Biopharmaceuticals," Drug Discovery Today (2010) 15 (17/18):773-780.
Wood, J.P., et al., "Tissue Factor Pathway Inhibitor-alpha Inhibits Prothrombinase During the Initiation of Blood Coagulation," PNAS (2013) 110(44):17838-17843.
Bunce, M.W., et al., "Restoring the Procofactor State of Factor Va-like Variants by Complementation with B-domain Peptides," J. Biol. Chem. (2013) 288(42):30151-30160.
Zhu, H., et al , "Inhibitory Sequences within the B-domain Stabilize Circulating Factor V in an Inactive State," J. Biol. Chem. (2007) 282(20):15033-15039.
Bos, M.H., et al., "A Bipartite Autoinhibitory Region within the B-domain Suppresses Function in Factor V," J. Biol. Chem. (2012) 287(31):26342-26351.
Toso, R., et al., "Removal of B-domain Sequences from Factor V Rather than Specific Proteolysis Underlies the Mechanism by which Cofactor Function Is Realized," J. Biol. Chem. (2004) 279(20):21643-21650.
Camire, R.M., et al., "The Molecular Basis of Factor V and VIII Procofactor Activation," J. Thromb. Haemost. (2009) 7(12)1951-1961.
Bunce, M.W., et al., "Modulating the Factor V Procofactor to Cofactor Transition Using Recombinant B-Domain Fragments," Blood (2011) 118:Abstract 376 [Abstract only].

\* cited by examiner

*Primary Examiner* — Amber D Steele
(74) *Attorney, Agent, or Firm* — Robert C. Netter, Jr.; Dann, Dorfman, Herrell & Skillman

(57) ABSTRACT

Factor V peptides and methods of use thereof are disclosed.

11 Claims, 17 Drawing Sheets

Specification includes a Sequence Listing.

Factor V

```
     A1        A2                A3    C1   C2
1 ─┤   ├──┤   ├──────────┤         ├──┤ ├──┤ ├─ 2196
         710   ↑        1545
              836 a.a.
```

```
903  L L L K Q S N S S K I L V G R W H L A S E K G S Y  928
     E I I Q D T D E D T A V N N W L I S P Q N A S R A W
955  G E S T P L A N K P G K Q S G H P K F P R V R H K S  980
     L Q V R Q D G G K S R L K K S Q F L I K T R K K K
1007 E K H T H H A P L S P R T F H P L R S E A Y N T F S E 1033
```

|              | 963 |   |   |   |   |   |   |   |   |   |   | 1008 |
|---|---|---|---|---|---|---|---|---|---|---|---|---|
| H. sapiens | K | · · P G K · · · Q S G · H P K F P R V · · · R H K · · S L Q V · · · · R · · · · · · Q · · · D G · G K S R L K K S Q F L I K T R K K K E · · K |
| S. scrofa | K | · · H G K · · · Q R G · H P I F · · V T · · · R H K · · L L Q E · · · · R · · · · · · Q · · · D E · G N S I L K K G R F F I R T R K K K E R · K |
| B. taurus | K N S H G K · · · Q S G · H P T F L · V T · · · R R K · · P L Q D · · · · Q · · · · · · Q · · · D R · R N S R L K E G L P L I R T R K K K E E · K |
| M. musculus | R · · · K · · · · P S D · L P T F S G V · · · G H K · · S P H V · · · · R · · · · · · Q · · · E E · E N S G F Q K R Q L F I R T R K K K N K · K |
| O. anatinus | R · · · Q G R · · · P V S · H Q K F A · E H · · R Q K · · I K R A · · · R P K F L N Q G A D G · E S T P I R P A M T F I K T R K K K I D · · K |
| G. gallus | K · · H H K K · K D G E F S H L M G E · · K H K G N H M R S P L K R · · · · K · · E G N K N D T L S I S G T F V K I R R K K K E Y P K |
| A. carolinensis | K · · K N K K A Y K E N S L P E L · G Q A E I N N K · · · · · N K V · L · N · · · · E · · Q R · Y E N S · S · S G T F I K I · R R K · · E · · K |
| X. tropicalis | K · · T Q E E · Q N A K K P T K · · · · · · R Y · · · · F Q V · · · · R P · · · I R · Y R T S S N · · E T R M L T R R K K R · · · · |
| D. rerio | K Y V K D K S A · A N S N K P K I E · · · · · K E K · · · · K K V · · · · Y · · · · Q R · V K P K · K · · G Y G M K T K K S K · D Y · K |
| T. rubripes | K · · · · · · Y F E M S P Q T N · · · · · · · · · · · T R K V · · · · · · · · · · · · N R P H R P Q · K · · G H G M K T K R R K · E Y · K |

Figure 1

COMPOSITIONS AND METHODS FOR MODULATING THROMBIN GENERATION

This application is a divisional of U.S. patent application Ser. No. 14/250,840, filed Apr. 11, 2014, which is a continuation-in-part of PCT/US2012/060232, filed on Oct. 15, 2012, which claims priority under 35 U.S.C. § 119(e) to U.S. Provisional Patent Application No. 61/546,752, filed Oct. 13, 2011. The foregoing applications are incorporated by reference herein.

This invention was made with government support under Grant Numbers R01HL088010 awarded by the National Institutes of Health. The government has certain rights in the invention.

FIELD OF THE INVENTION

The present invention relates to the fields of medicine and hematology. More specifically, the invention provides novel Factor V peptides and methods of using the same to modulate the coagulation cascade in patients in need thereof.

BACKGROUND OF THE INVENTION

Several publications and patent documents are cited throughout the specification in order to describe the state of the art to which this invention pertains. Each of these citations is incorporated herein by reference as though set forth in full.

In response to vascular injury such as a cut, coagulation enzymes are activated in a stepwise manner, ultimately resulting in the formation of a blood clot at the site of injury. Thrombin is generated from its inactive precursor prothrombin in the final step of this cascade and subsequently produces the fibrous clot. Prothrombinase, the enzyme complex that activates thrombin, consists of the protease Factor Xa (FXa) and its non-enzymatic cofactor, activated Factor V (FVa), which assemble on phospholipid membrane surfaces near the injury. FVa is critical for thrombin generation, as FXa has very little activity in the absence of FVa. Like other proteins of the coagulation cascade, the active cofactor FVa is generated from an inactive precursor, Factor V (FV) which is an inactive procofactor. FV activation occurs by removal of a large inhibitory "B" domain as two fragments (~71 kDa and ~150 kDa) that maintains FV in an inactive state. Accordingly, the inhibition of FV activation or stabilization of the inactive procofactor state is desired in order to reduce improper or unwanted thrombin generation and clot formation.

SUMMARY OF THE INVENTION

In accordance with the instant invention, Factor V peptides for the modulation of thrombin generation are provided. In a particular embodiment, the peptide has at least 80% homology with SEQ ID NO: 1, 2, 3 or 4. Nucleic acid molecules encoding the peptides are also encompassed by the instant invention. Compositions comprising at least one peptide and/or nucleic acid of the instant invention and at least one pharmaceutically acceptable carrier are also provided. The compositions may further comprise at least one other anti-thrombosis compound.

According to another aspect of the instant invention, methods for inhibiting, treating, and/or preventing clot formation in a subject in need thereof are provided. Methods for inhibiting, treating, and/or inhibiting a hemostasis disorder in a patient in need thereof are provided. In a particular embodiment, the methods comprise administering to the subject at least one composition of the instant invention. The methods may further comprise administering at least one additional anti-thrombosis compound.

BRIEF DESCRIPTION OF THE DRAWINGS

FIG. 1 provides a schematic of Factor V with the amino acid sequence of a conserved basic region within the B domain (SEQ ID NO: 5). A sequence alignment of the conserved basic region across various species is also provided. Sequences are SEQ ID NOs: 6-15, from top to bottom.

FIG. 2A is a graph of a titration of the FV basic peptide (FVBR) inhibiting activation of prothrombin by FXa/FVDT but not FXa/FVa. FIG. 2B shows the activity of FVDT and other variants in clotting assays in the presence of FVBR or the control peptide (s46). FIG. 2C provides schematics of various FV-810 variants and their cleavage products. FIG. 2C also provides a graph of the activity of FVDT and these variants in clotting assays in the presence or absence of FVBR and the presence or absence of thrombin (IIa). FIG. 2D shows the clot time of normal human plasma with increasing amounts of FVBR.

FIG. 3A shows the binding of fluorescently-labeled FXa to FVDT on liposomes in the presence or absence of FVBR. FIG. 3B shows the binding of FXa to FVDT or FVa in the presence of different concentrations of FVBR. FIG. 3C shows the direct binding of fluorescently labeled FVBR to FVDT.

FIGS. 4A and 4B provide images of the cleavage of FV over time in the absence or presence of FVBR, respectively. B+LC=B domain and light chain. HC=heavy chain. LC=light chain.

FIG. 12A: FXaS195A (●) or zymogen FXS195A (▲) was titrated into reaction mixtures containing 30 nM OG488-BR, 20 nM FV-810, and 50 µM PCPS in assay buffer at 25° C. Changes in OG488-BR anisotropy were measured, and lines were drawn with the fitted constants Kd=1.8±0.2 nM for FXa and n=1.1±0.07 mol of FXa/mol of FV-810. FIG. 12B: Reactions containing 1.4 µM prethrombin-2, 3 µM DAPA, 50 µM PCPS, 5 nM FV-810, and 0 nM (■), 125 nM (●), 250 nM (▲), 500 nM (♦), or 1 µM (▼) BR peptide were prepared in assay buffer at 25° C. Reactions were initiated by the addition of 1-50 nM FXa, and thrombin generation was monitored. Experimental data were fitted to a model for tight binding with calculated values of Kd=2.0±0.2 nM for FXa and Kd=34.2±3.6 nM for the BR.

DETAILED DESCRIPTION OF THE INVENTION

Figure 2A:
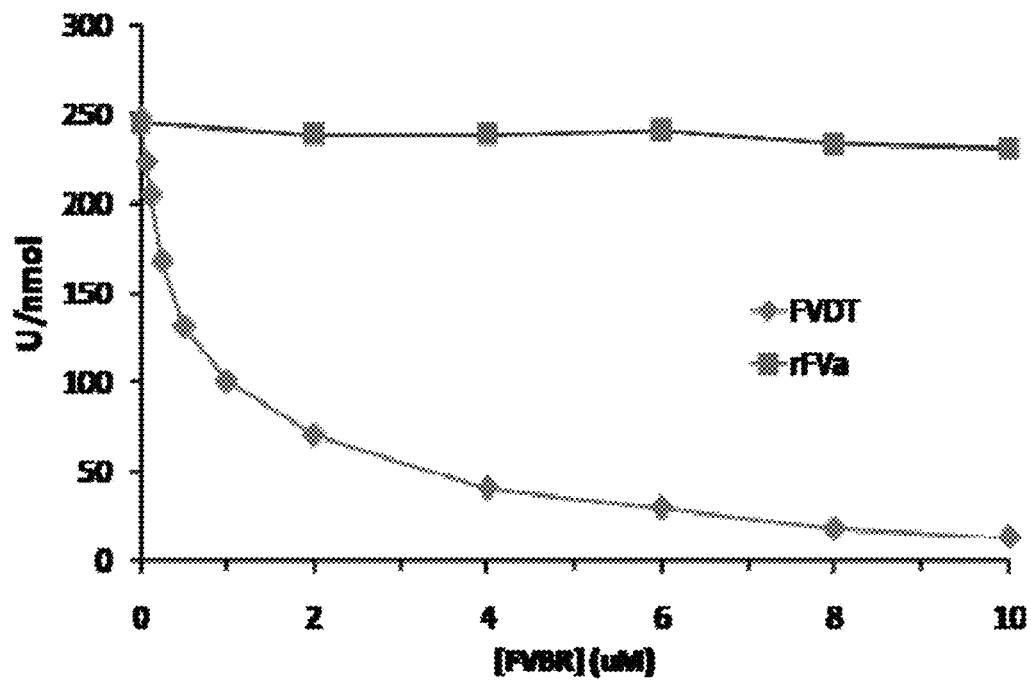
FIGS. 2A-2D provide graphs showing that a FV basic region peptide inhibits multiple cofactor-like FV variants.

Herein, peptides that inhibit the generation of the clotting enzyme thrombin are provided. Specifically, a region of approximately 50 amino acids within the FV B domain (963-1008) has been identified that is required to keep FV inactive. This region is enriched with the basic amino acids arginine and lysine, giving it a strong positive net charge at physiological pH. Removal of this region (the FV basic region) switches FV from an inactive procofactor to an active, FVa-like cofactor that rescues thrombin generation. Without being bound by theory, the data provided herein indicate that the basic region functions at least by interacting with a highly acidic region at the C-terminal end of the B domain (1493-1537) and that this interaction maintains FV in an inactive state. When added to reactions as a separate peptide, the FV basic region inhibits cofactor-like FV variants that contain the acidic region, rendering them procofactor-like and inhibiting thrombin generation. Furthermore, the FV basic region peptide substantially impairs the ability of thrombin to proteolytically convert FV to FVa, an important feedback step of the coagulation cascade in vivo. These data indicate that the FV basic region peptides of the instant invention effectively inhibit FV by maintaining the inactive, procofactor-like state, thereby reducing thrombin generation and clot formation.

Peptides

Peptides of the present invention may be prepared in a variety of ways, according to known methods. The proteins may be purified from appropriate sources, e.g., transformed bacterial or animal cultured cells or tissues. The availability of nucleic acid molecules encoding the peptides of the instant invention enables production of the protein using in vitro expression methods and cell-free expression systems known in the art. In vitro transcription and translation systems are commercially available, e.g., from Promega Biotech (Madison, Wis.) or Gibco-BRL (Gaithersburg, Md.).

Larger quantities of peptides of the instant invention may be produced by expression in a suitable prokaryotic or eukaryotic system. For example, part or all of a DNA molecule encoding for the peptides of the instant invention may be inserted into a plasmid vector adapted for expression in a bacterial cell, such as *E. coli*. Such vectors comprise the regulatory elements necessary for expression of the DNA in the host cell positioned in such a manner as to permit expression of the DNA in the host cell. Such regulatory elements required for expression include promoter sequences, transcription initiation sequences and, optionally, enhancer sequences.

Peptides of the instant invention produced by gene expression in a recombinant prokaryotic or eukaryotic system may be purified according to methods known in the art.

A commercially available expression/secretion system can be used, whereby the recombinant protein is expressed and thereafter secreted from the host cell, and readily purified from the surrounding medium. The recombinant protein may also be purified by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise the FLAG epitope or the hemagglutinin epitope. Such methods are commonly used by skilled practitioners.

Peptides of the instant invention may also be made by peptide synthesis. For example, the peptides may be made by liquid-phase peptide synthesis or solid-phase peptide synthesis (SPPS).

Peptides of the instant invention, prepared by the aforementioned methods, may be analyzed according to standard procedures. For example, such protein may be subjected to amino acid sequence analysis, according to known methods.

Examples of amino acid sequences of the peptides of the instant invention include SRAWGESTPLANKPGKQSGH-PKFPRVRHKSLQVRQDGGKSRLKKSQFLIKTRKK KKEK (SEQ ID NO: 1), KPGKQSGHPKFPRVRHK-SLQVRQDGGKSRLKKSQ FLIKTRKKKKEK (SEQ ID NO: 2), RQDGGKSRLKKSQFLIKTRKKKKEK (SEQ ID NO: 3), and KKGFIQRISKGGLIKTKRKRKKQRVK (SEQ ID NO: 4). The amino acid sequence of the peptides of the instant invention may have at least 75%, 80%, 85%, 90%, 95%, 97%, 99%, or 100% homology (identity) with SEQ ID NO: 1, 2, 3 or 4, particularly at least 90% homology. In a particular embodiment, the peptide is a fragment of SEQ ID NO: 1, 2, 3, or 4. For example, the peptide fragment may comprise at least about 20, about 25, about 30, about 35, about 40, about 45, about 50, or about 55 contiguous amino acids of SEQ ID NO: 1, 2, 3, or 4. In a particular embodiment, the peptide fragment is a fragment of SEQ ID NO: 1, but comprises SEQ ID NO: 2 or 3.

In a particular embodiment, the peptide of the instant invention has a length of about 10 to about 100, about 20 to about 80 amino acids, about 20 to about 60, about 25 to about 60, about 30 to about 70 amino acids, or about 40 to about 60 amino acids. As stated hereinabove, the peptides of the instant invention may comprise a sequence having at least 75%, 80%, 85%, 90%, 95%, 97%, 99%, or 100% homology (identity) with SEQ ID NO: 1, 2, 3, or 4 or a fragment thereof. The peptides of the instant invention may extend beyond SEQ ID NO: 1, 2, 3, or 4 or a fragment thereof at either the amino or carboxy terminus. The sequence extension at either end may be of any sequence. In a particular embodiment, the extension sequence comprises basic amino acids. In a particular embodiment, the extension sequence corresponds to the B domain sequence of Factor V (e.g., for SEQ ID NO: 3) or TFPI (e.g., for SEQ ID NO: 4). For example, if the sequence extends three amino acids C-terminal to SEQ ID NO: 1, the sequence of the three amino acid extension may be HTH, which corresponds to amino acids 1009-1011 of the B domain.

The peptides of the instant invention may contain at least one substitution, addition, or insertion to the amino acids of SEQ ID NO: 1, 2, 3, or 4. These substitutions may be conservative—i.e., similar to the amino acid present in SEQ ID NO: 1, 2, 3 or 4 (e.g., an acidic amino acid in place of another acidic amino acid, a basic amino acid in place of a basic amino acid, a large hydrophobic amino acid in place of a large hydrophobic, etc.). The substitutions may comprise amino acid analogs and mimetics. In a particular embodiment, the substitution(s) and/or addition(s) increases the number of basic amino acids present in the peptide. In a particular embodiment, the substitutions increase the affinity of the peptide for the conserved acidic region of the B domain (see FIG. 5).

The peptides of the instant invention may have capping, protecting and/or stabilizing moieties, for example at the C-terminus and/or N-terminus. Such moieties are well known in the art and include, without limitation, amidation or esterification of the carboxy-terminal end and acylation or acetylation of the amino-terminal end. The peptide may also be PEGylated. The peptide may also be lipidated or glycosylated at any amino acid (i.e., a glycopeptide). The peptides of the instant invention may also comprise at least one D-amino acid instead of the native L-amino acid. The peptides may comprise only D-amino acids.

The peptides of the instant invention can be based on a Factor V from any species, particularly a mammalian Factor V, more particularly a human Factor V. FIG. 1 provides examples of the Factor V basic domain from various species. GenBank Accession No. NP_000121.2 provides an example of the wild-type human FV precursor protein wherein amino acids 1-28 are a signal peptide that is cleaved and numbering begins at residue 29. The peptides of the instant invention can also be based on a TFPI from any species, particularly a mammalian TFPI, more particularly a human TFPI. GenBank Accession No. NP_006278.1 provides an example of the wild-type human TFPI precursor protein wherein amino acids 1-28 are a signal peptide that is cleaved and numbering begins at residue 29.

Compositions comprising at least one peptide and at least one carrier are also encompassed by the instant invention. Except insofar as any conventional carrier is incompatible with the peptide to be administered, its use in the pharmaceutical composition is contemplated. In a particular embodiment, the carrier is a pharmaceutically acceptable carrier for intravenous administration.

Nucleic Acid Molecules

Nucleic acid molecules encoding the peptides of the invention may be prepared by any method known in the art such as (1) synthesis from appropriate nucleotide triphosphates or (2) isolation and/or amplification from biological sources. The availability of nucleotide sequence information enables preparation of an isolated nucleic acid molecule of the invention by oligonucleotide synthesis. Indeed, knowledge of the amino sequence is sufficient to determine an encoding nucleic acid molecule. Synthetic oligonucleotides may be prepared by the phosphoramidite method employed in the Applied Biosystems 38A DNA Synthesizer or similar devices. The resultant construct may be purified according to methods known in the art, such as gel electrophoresis or high performance liquid chromatography (HPLC).

Nucleic acids of the present invention may be maintained in any convenient vector or viral vector, particularly an expression vector. Different promoters may be utilized to drive expression of the nucleic acid sequences based on the cell in which it is to be expressed. Antibiotic resistance markers are also included in these vectors to enable selection of transformed cells. Peptide encoding nucleic acid molecules of the invention include cDNA, genomic DNA, DNA, RNA, and fragments thereof which may be single- or double-stranded. Thus, this invention provides oligonucleotides having sequences capable of hybridizing with at least one sequence of a nucleic acid molecule of the present invention.

Also encompassed in the scope of the present invention are oligonucleotide probes which specifically hybridize with the peptide encoding nucleic acid molecules of the invention. Primers capable of specifically amplifying peptide encoding nucleic acids described herein are also contemplated herein. Such oligonucleotides are useful as probes and primers for detecting, isolating or amplifying peptide encoding nucleic acids.

It will be appreciated by persons skilled in the art that variants (e.g., allelic variants) of Factor V sequences exist, for example, in the human population, and may be taken into account when designing and/or utilizing oligonucleotides or peptides of the invention. Accordingly, it is within the scope of the present invention to encompass such variants, with respect to the peptide sequences disclosed herein or the oligonucleotides targeted to specific locations on the respective genes or RNA transcripts. Accordingly, the term "natural allelic variants" is used herein to refer to various specific nucleotide sequences of the invention and variants thereof that would occur in a human population. The usage of different wobble codons and genetic polymorphisms which give rise to conservative or neutral amino acid substitutions in the encoded protein are examples of such variants. Such variants would not demonstrate substantially altered activity or protein levels.

Compositions comprising at least one nucleic acid molecule of the instant invention (e.g., a vector) and at least one carrier are also encompassed by the instant invention. The compositions of the instant invention may be used, for example, as therapeutic and/or prophylactic agents (protein or nucleic acid) which modulate the blood coagulation cascade. It is demonstrated herein that the peptides can inhibit clot formation and effect hemostasis.

Uses

The instant invention encompasses methods of inhibiting and/or preventing clot formation. The instant invention also encompasses methods of treating and/or inhibiting hemostasis disorders, particularly disorders with aberrant, excessive, or improper coagulation. Examples of such hemostasis disorders include, without limitation, thrombosis, deep venous thrombosis, thrombosis associated with cardiovascular disease, thrombosis associated with a malignancy, thrombosis resulting from invasive surgical devices (e.g., catheters, cardiac catheter, intravascular catheter, intra-aortic balloon pump, coronary stent, or cardiac valve), thrombosis associated with autoimmune diseases (e.g., lupus), thrombocytopenia (e.g., heparin-induced), stroke (e.g., embolic stroke, thrombotic stroke), coagulopathy. The peptides can provide necessary anticoagulant treatment for patients with disseminated intravascular coagulation or consumptive coagulopathies arising from a variety of disease or disorder states. The peptides can provide necessary anticoagulant treatment for patients suffering from myocardial infarction.

In a particular embodiment of the present invention, peptides of the instant invention may be administered to a patient in a pharmaceutically acceptable carrier, particularly via intravenous injection. The peptides of the instant invention may optionally be encapsulated into liposomes or mixed with other phospholipids or micelles to increase stability of the molecule. Peptides may be administered alone or in combination with other agents known to modulate hemostasis (e.g., agents which inhibit clot formation). For example, the compositions of the instant invention may be co-administered with other anti-thrombosis compounds. Examples of anti-thrombosis compounds include, without limitation, vitamin K antagonists (e.g., warfarin, acenocoumarol, dicumarol, phenprocoumon, related 4-hydroxycoumarin-containing molecules, phenindione, and inhibitors of vitamin K epoxide reductase), direct thrombin inhibitors (DTIs; e.g., hirudin, bivalirudin, lepirudin, argatroban, ximelagatran, melagatran, and dabigatran), Factor Xa inhibitors (e.g., heparin, low molecular weight heparin, certoparin, dalteparin, enoxaparin, nadroparin, tinzaparin, reviparin, parnaparin, bemiparin, fondaparinux, idraparinux, heparinoid, danaparoid, sulodexide, xabans, apixaban, betrixaban, edoxaban, otamixaban, and rivaroxaban), defibrotide, and anti-platelet agents (e.g., glycoprotein IIb/IIIa inhibitors (e.g., abciximab, eptifibatide, tirofiban), ADP receptor/$P2Y_{12}$ inhibitors (e.g., thienopyridines (e.g., clopidogrel, prasugrel, and ticlopidine) and nucleotide/nucleoside analogs (e.g., cangrelor, elinogrel, and ticagrelor); prostaglandin analogue (e.g., beraprost, prostacyclin, iloprost, and treprostinil); COX inhibitors (e.g., acetylsalicylic acid/aspirin, carbasalate calcium, indobufen, and triflusal); thromboxane inhibitors (e.g., thromboxane synthase inhibitors such as dipyridamole or picotamide) and receptor antagonists such as terutroban); phosphodiesterase inhibitors (e.g., cilostazol, dipyridamole, and triflusal). The anti-thrombosis compound may be in the same composition comprising the peptide of the instant invention or may be in a separate composition. The compositions may be administered concurrently or consecutively. Kits comprising at least one first composition comprising at least one peptide of the instant invention and at least one second composition comprising at least one other anti-thrombosis compound are encompassed by the instant invention.

An appropriate composition in which to deliver peptides may be determined by a medical practitioner upon consideration of a variety of physiological variables, including, but not limited to, the patient's condition and hemodynamic state. A variety of compositions well suited for different applications and routes of administration are well known in the art and are described hereinbelow.

The preparation containing the purified peptides contains a physiologically acceptable matrix and is preferably formulated as a pharmaceutical preparation. The preparation can be formulated using substantially known prior art methods, it can be mixed with a buffer containing salts, such as $NaCl$, $CaCl_2$, and amino acids, such as glycine and/or lysine, and in a pH range from 6 to 8. Until needed, the purified preparation containing the peptide can be stored in the form of a finished solution or in lyophilized or deep-frozen form. In a particular embodiment, the preparation is stored in lyophilized form and is dissolved into a visually clear solution using an appropriate reconstitution solution. Alternatively, the preparation according to the present invention can also be made available as a liquid preparation or as a liquid that is deep-frozen. The preparation according to the present invention is especially stable, i.e., it can be allowed to stand in dissolved form for a prolonged time prior to application.

Prior to processing the purified protein into a pharmaceutical preparation, the purified peptide may be subjected to the conventional quality controls and fashioned into a therapeutic form of presentation. In particular, during the recombinant manufacture, the purified preparation may be tested for the absence of cellular nucleic acids as well as nucleic acids that are derived from the expression vector.

Peptide-encoding nucleic acids may be used for a variety of purposes in accordance with the present invention. In a particular embodiment of the invention, a nucleic acid delivery vehicle (i.e., an expression vector) for modulating blood coagulation is provided wherein the expression vector comprises a nucleic acid sequence coding for a peptide of the instant invention. Administration of peptide-encoding expression vectors to a patient results in the expression of peptide which serves to alter the coagulation cascade.

Expression vectors comprising peptide nucleic acid sequences may be administered alone, or in combination with other molecules useful for modulating hemostasis. According to the present invention, the expression vectors or combination of therapeutic agents may be administered to the patient alone or in a pharmaceutically acceptable or biologically compatible composition.

In a particular embodiment of the invention, the expression vector comprising nucleic acid sequences encoding the peptide is a viral vector. Viral vectors which may be used in the present invention include, but are not limited to, adenoviral vectors (with or without tissue specific promoters/enhancers), adeno-associated virus (AAV) vectors of multiple serotypes (e.g., AAV-2, AAV-5, AAV-7, and AAV-8) and hybrid AAV vectors, lentivirus vectors and pseudotyped lentivirus vectors (e.g., Ebola virus, vesicular stomatitis virus (VSV), and feline immunodeficiency virus (FIV)), herpes simplex virus vectors, vaccinia virus vectors, and retroviral vectors.

In a particular embodiment of the present invention, methods are provided for the administration of a viral vector comprising nucleic acid sequences encoding peptides of the instant invention. Adenoviral vectors of utility in the methods of the present invention preferably include at least the essential parts of adenoviral vector DNA. As described herein, expression of a peptide following administration of such an adenoviral vector serves to modulate hemostasis. Recombinant adenoviral vectors have found broad utility for a variety of gene therapy applications. Their utility for such applications is due largely to the high efficiency of in vivo gene transfer.

The expression vectors of the present invention may be incorporated into pharmaceutical compositions that may be delivered to a subject, so as to allow production of a biologically active peptide. In a particular embodiment of the present invention, pharmaceutical compositions comprising sufficient genetic material to enable a recipient to produce a therapeutically effective amount of a peptide can influence hemostasis in the subject. Alternatively, as discussed above, an effective amount of the peptide may be directly injected into a patient in need thereof. The compositions may be administered alone or in combination with at least one other agent, such as a stabilizing compound, which may be administered in any sterile, biocompatible pharmaceutical carrier, including, but not limited to, saline, buffered saline, dextrose, and water. The compositions may be administered to a patient alone, or in combination with other agents which influence hemostasis.

In particular embodiments, the pharmaceutical compositions also contain a pharmaceutically acceptable excipient/carrier. Such excipients include any pharmaceutical agent that does not itself induce an immune response harmful to the individual receiving the composition, and which may be administered without undue toxicity. Pharmaceutically acceptable excipients include, but are not limited to, liquids such as water, saline, glycerol, sugars and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in Remington's Pharmaceutical Sciences (Mack Pub. Co., Easton, Pa.).

Pharmaceutical compositions suitable for use in the invention include compositions wherein the active ingredients are contained in an effective amount to achieve the intended therapeutic purpose. Determining a therapeutically effective dose is well within the capability of a skilled medical practitioner using the techniques and guidance provided in the present invention. Therapeutic doses will depend on, among other factors, the age and general condition of the subject, the severity of the aberrant blood coagulation phenotype, and the strength of the control sequences regulating the expression levels of the peptide. Thus, a therapeutically effective amount in humans will fall in a relatively broad range that may be determined by a medical practitioner based on the response of an individual patient to peptide treatment.

Direct delivery of the pharmaceutical compositions in vivo may generally be accomplished via injection using a conventional syringe. The compositions of the instant invention may be delivered subcutaneously, epidermally, intradermally, intrathecally, intraorbitally, intramucosally, intraperitoneally, intravenously, intraarterially, orally, intrahepatically or intramuscularly. A clinician specializing in the treatment of patients with blood coagulation disorders may determine the optimal route for administration of the compositions of the instant invention based on a number of criteria, including, but not limited to: the condition of the patient and the purpose of the treatment (e.g., reduced blood coagulation).

Definitions

Various terms relating to the biological molecules of the present invention are used hereinabove and also throughout the specification and claims.

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it originates. For example, the "isolated nucleic acid" may comprise a DNA or cDNA molecule inserted into a vector, such as a plasmid or virus vector, or integrated into the DNA of a prokaryote or eukaryote.

With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

The term "oligonucleotide" as used herein refers to sequences, primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as appropriate temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 10-30 or 15-25, or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 10-30 or 15-25, or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., 1989, Molecular Cloning: A Laboratory Manual, Cold Spring Harbor Laboratory Press):

$$Tm=81.5° C.+16.6 \text{ Log } [Na+]+0.41(\% G+C)-0.63(\% \text{ formamide})-600/\#bp \text{ in duplex}$$

As an illustration of the above formula, using [Na+]= [0.368] and 50% formamide, with GC content of 42% and an average probe size of 200 bases, the Tm is 57° C. The Tm of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20 25° C. below the calculated Tm of the hybrid. Wash conditions should be as stringent as possible for the degree of identity of the probe for the target. In general, wash conditions are selected to be approximately 12 20° C. below the Tm of the hybrid. In regards to the nucleic acids of the current invention, a moderate stringency hybridization is defined as hybridization in 6×SSC, 5×Denhardt's solution, 0.5% SDS and 100 μg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 μg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 μg/ml denatured salmon sperm DNA at 42° C., and washed in 0.1×SSC and 0.5% SDS at 65° C. for 15 minutes.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, or the addition of stabilizers.

The term "vector" refers to a carrier nucleic acid molecule (e.g., DNA) into which a nucleic acid sequence can be inserted for introduction into a host cell where it will be replicated. An "expression vector" is a specialized vector that contains a gene or nucleic acid sequence with the necessary regulatory regions needed for expression in a host cell.

The term "operably linked" means that the regulatory sequences necessary for expression of a coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The term "substantially pure" refers to a preparation comprising at least 50-60% by weight the compound of interest (e.g., nucleic acid, oligonucleotide, protein, etc.), particularly at least 75% by weight, or at least 90-99% or more by weight of the compound of interest. Purity may be measured by methods appropriate for the compound of interest (e.g. chromatographic methods, agarose or polyacrylamide gel electrophoresis, HPLC analysis, and the like).

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween 80, Polysorbate 80), emulsifier, buffer (e.g., Tris HCl, acetate, phosphate), antimicrobial, bulking substance (e.g., lactose, mannitol), excipient, auxiliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients, American Pharmaceutical Association, Washington.

As used herein, a "conservative" amino acid substitution/mutation refers to substituting a particular amino acid with an amino acid having a side chain of similar nature (i.e., replacing one amino acid with another amino acid belonging to the same group). A "non-conservative" amino acid substitution/mutation refers to replacing a particular amino acid with another amino acid having a side chain of different nature (i.e., replacing one amino acid with another amino acid belonging to a different group). Groups of amino acids having a side chain of similar nature are known in the art and include, without limitation, basic amino acids (e.g., lysine, arginine, histidine); acidic amino acids (e.g., aspartic acid, glutamic acid); neutral amino acids (e.g., glycine, asparagine, glutamine, serine, threonine, tyrosine, cysteine, alanine, valine, leucine, isoleucine, proline, phenylalanine, methionine, tryptophan); amino acids having a polar side chain (e.g., glycine, asparagine, glutamine, serine, threonine, tyrosine, cysteine); amino acids having a non-polar side chain (e.g., alanine, valine, leucine, isoleucine, proline, phenylalanine, methionine, tryptophan); amino acids having an aromatic side chain (e.g., phenylalanine, tryptophan, histidine); amino acids having a side chain containing a hydroxyl group (e.g., serine, threonine, tyrosine), and the like.

The following examples are provided to illustrate various embodiments of the present invention. The examples are illustrative and are not intended to limit the invention in any way.

EXAMPLE I

Materials and Methods
Factor V Peptide Expression and Purification cDNA for Factor V amino acids 951-1008 was amplified from full-length human Factor V cDNA using site-specific primers and was subcloned into the pE-SUMO bacterial expression vector (LifeSensors, Malvern Pa.). SUMO-FV (951-1008) fusion protein was expressed in BL21(DE3) *E. coli* and purified with HisTrap™ FF columns (Amersham). After incubating the purified fusion protein with SUMO Protease (LifeSensors), the FVBR peptide was purified by ion exchange chromatography. The control peptide s46 (derived from the s46 protein construct detailed in Zhu et al. (2007) JBC 282:15033-15039) and the TFPI C-terminal tail peptide (residues 240-276) were generated using a similar approach.

Prothrombin Activation Assays

Steady-state initial velocities of prothrombin cleavage were determined discontinuously at 25° C. by measuring the initial rate of thrombin formation. Reaction mixtures contained liposomes (75:25, PC:PS), prothrombin, the indicated Factor V variants, and the Factor V peptides FVBR or s46. The reactions were initiated by adding Factor Xa, and thrombin generation was determined at multiple time points by monitoring the cleavage of the chromogenic thrombin substrate S-2238.

Clotting Assays

Residual clotting activity of Factor V variants was determined by prothrombin time-based clotting assays. Factor V variants were incubated with either the FVBR or s46 peptide, after which the mixtures were mixed with Factor V deficient plasma and clotting times were measured. Where indicated, the Factor V variants were activated by pre-incubation with thrombin prior to addition of the peptides.

Proteolytic Activation of Factor V by Thrombin

Plasma-derived Factor V was incubated with thrombin in the presence or absence of FVBR peptide. Samples were removed and quenched in sample buffer at the indicated times, and the cleavage products were analyzed by SDS-PAGE and Coomassie Brilliant Blue staining.

Direct Binding Measurements

Figure 3A:
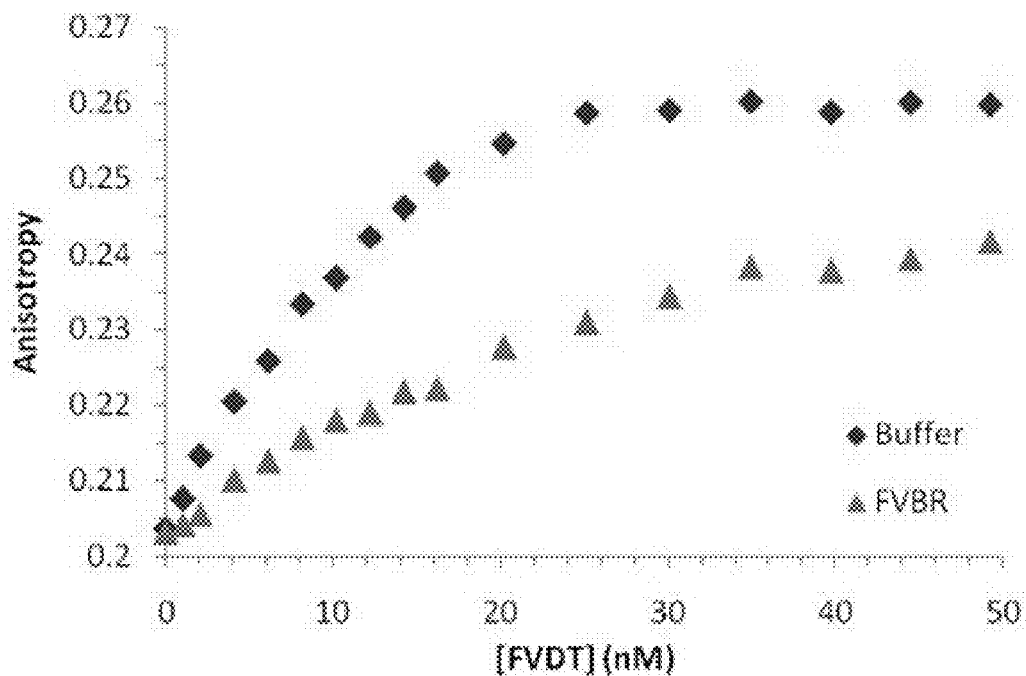
FIGS. 3A-3C provide graphs demonstrating that a FV basic region peptide binds FVDT and disrupts binding of FXa to FVDT but not to FVa.
Figure 3B:
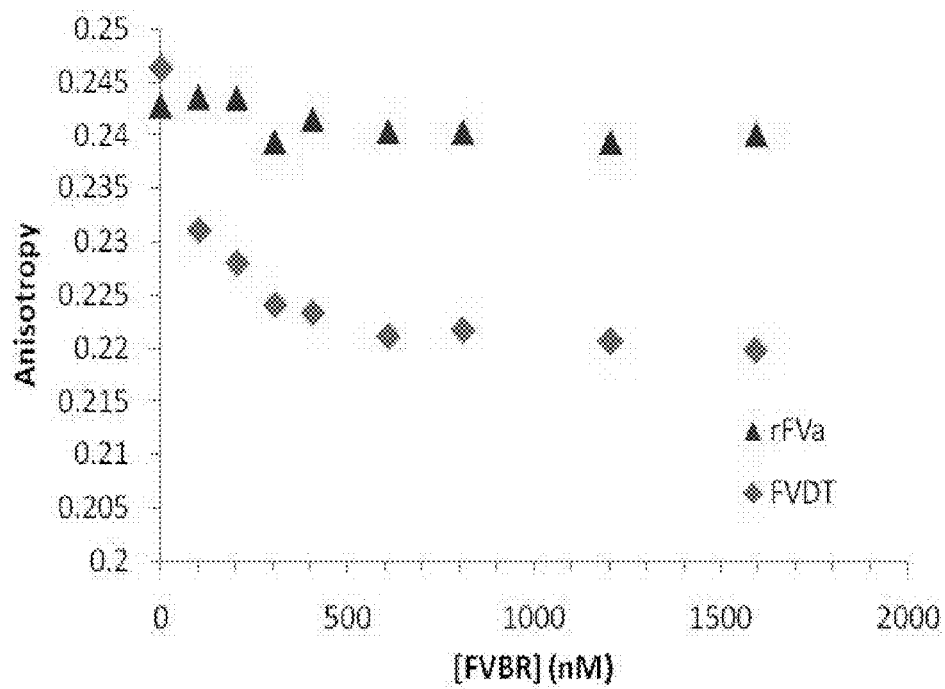

Fluorescently-labeled, active site-blocked FXa was incubated with PCPS liposomes and either FV-DT or rFVa in the absence of presence of FVBR peptide. The ability of the peptide to disrupt binding between FXa and FVDT or rFVa was assessed by monitoring the reduced change in anisotropy (FIG. 3A) or reduction in anisotropy resulting from disruption of the FXa/FVa complex (FIG. 3B).

Results

Figure 2B:
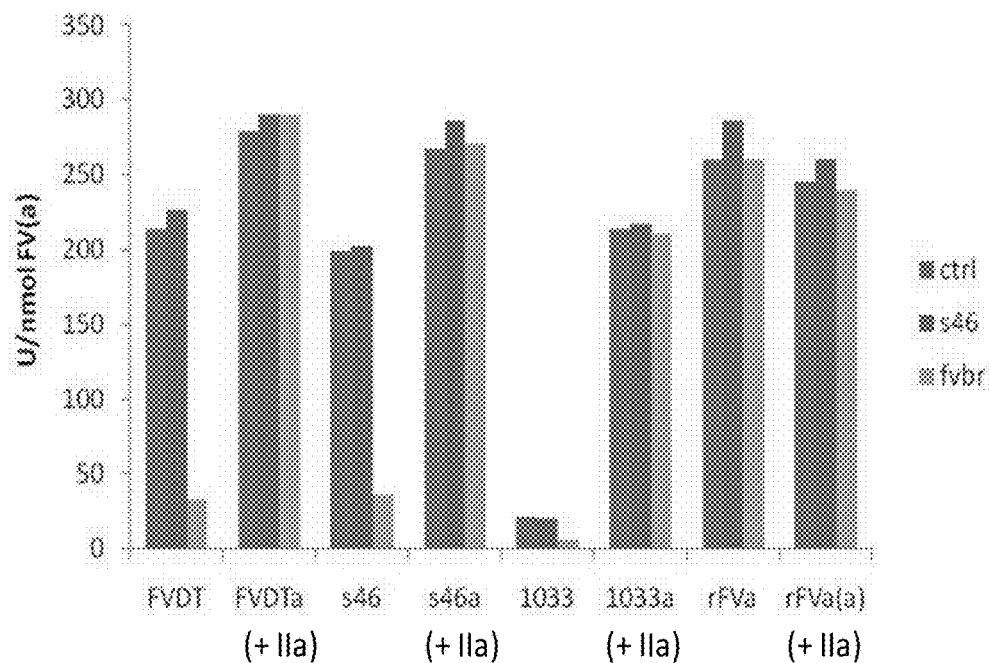
Figure 2C:
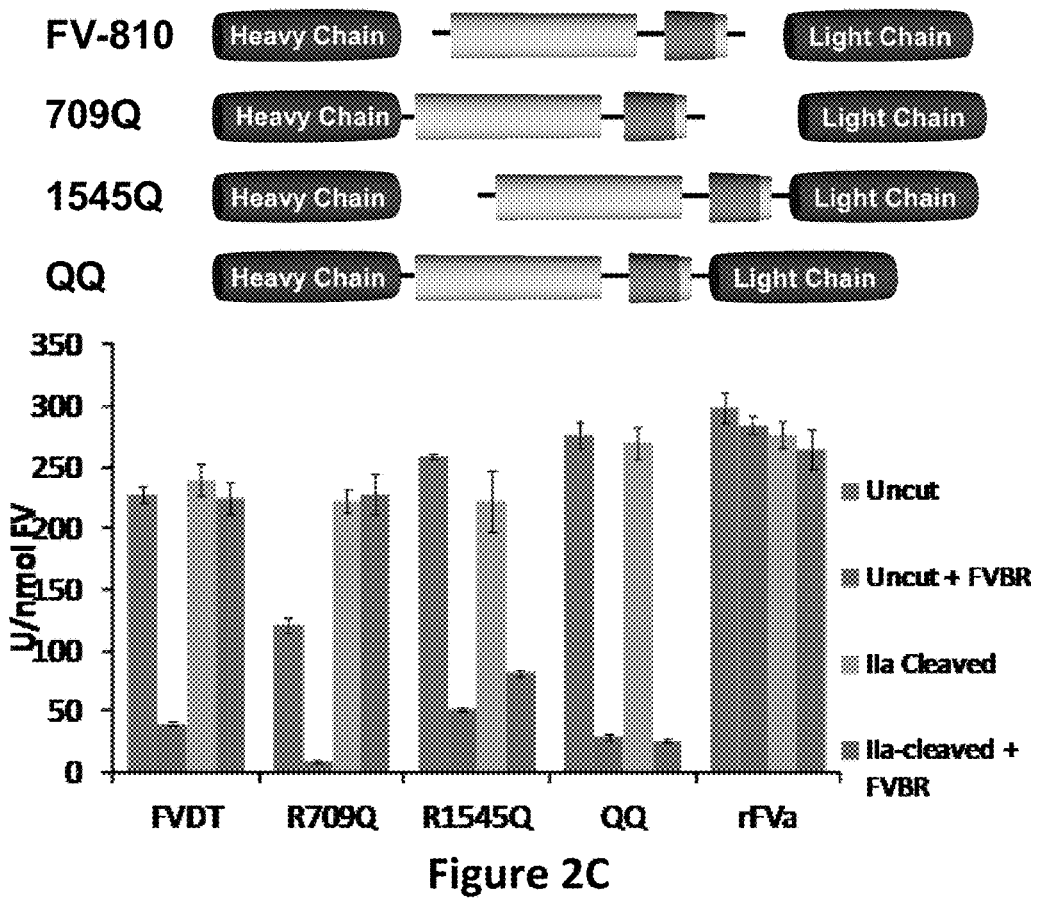
Figure 2D:
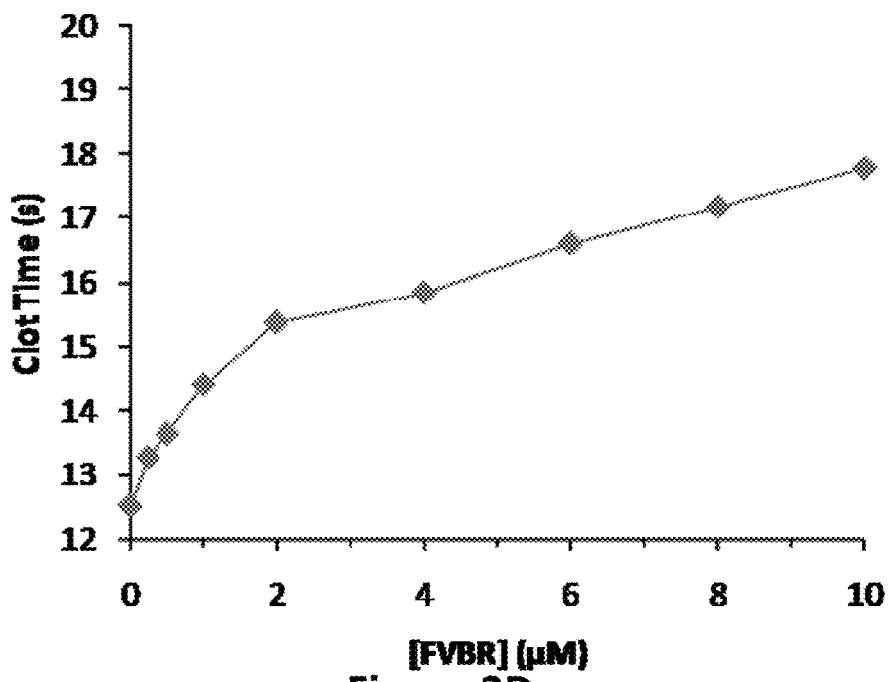

A Factor V basic peptide (FVBR) having the following sequence was synthesized: SRAWGESTPLANKPGKQS-GHPKFPRVRHKSLQVRQDGGKSRLKKSQFLIKTRKK KKEK (SEQ ID NO: 1), corresponding to amino acids 951-1008 of Factor V. The presence of the basic peptide FVBR did not affect activation of prothrombin by Factor Xa/FVa (FIGS. 2A and 2B). However, a titration of FVBR does show inhibition of the activation of prothrombin by FXa/FV-DT, where FV-DT is Factor V with amino acids 811-1491 deleted from the B-domain (FIGS. 2A and 2B). FV-DT harbors an important region in the truncated B-domain which is enriched in acidic amino acids (1493-1537; see FIG. 5). As seen in FIG. 2B, the basic peptide FVBR inhibited FV-DT and similar variants in clotting assays, but not FVa. The other variants tested include s46 (where amino acids 963-1008 from Factor V have been replaced with amino acids 1032-1077 from Factor VIII) and FV-1033, which is a Factor V lacking amino acids 1034-1491. Further, the control peptide s46, which corresponds to amino acids 1032-1077 of factor VIII, had no effect. Various FV-810 cleavage mutants were also tested (FIG. 2C). Specifically, the arginine at position 709, the arginine at position 1545, or both were changed to a glutamine to eliminate the thrombin cleavage sites. The ability of FVBR to inhibit these cleavage mutants is shown in FIG. 2C. The data show that the B-domain harboring the acidic region needs to be tethered to the light chain for the FVBR to effectively inhibit cofactor function. FIG. 2D shows that FVBR prolongs the clot time in normal plasma in a concentration dependent manner.

Figure 3C:
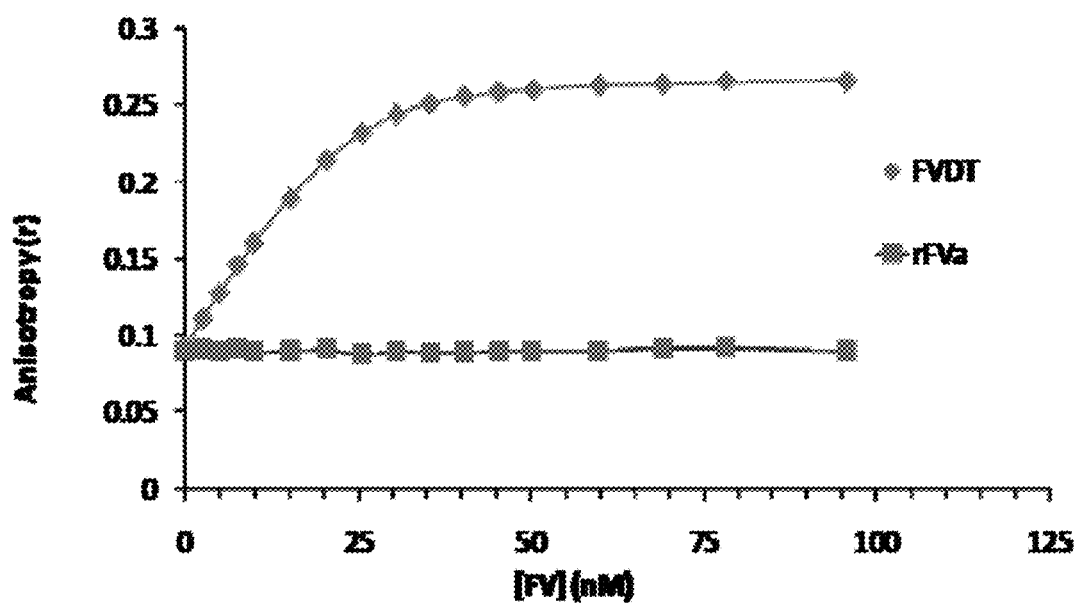

The FV basic region peptide was determined to disrupt the binding of FXa to FV-DT, but not to FVa. As seen in FIG. 3A, the binding of fluorescently labeled FXa to FV-DT on liposomes is impaired in the presence of FVBR. The disruption of the interaction with FXa by FVBR is observed only with FV-DT and not FVa (FIG. 3B). FIG. 3C shows the direct binding of FVBR to FVDT, but not FVa.

Figure 4A:
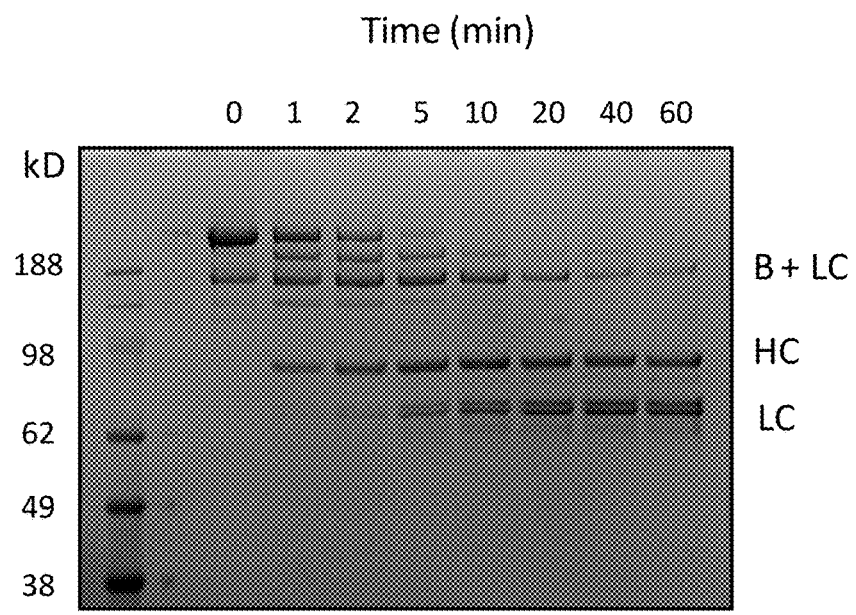
FIGS. 4A-4B show that FVBR delays the proteolytic activation of FV by thrombin.
Figure 4B:
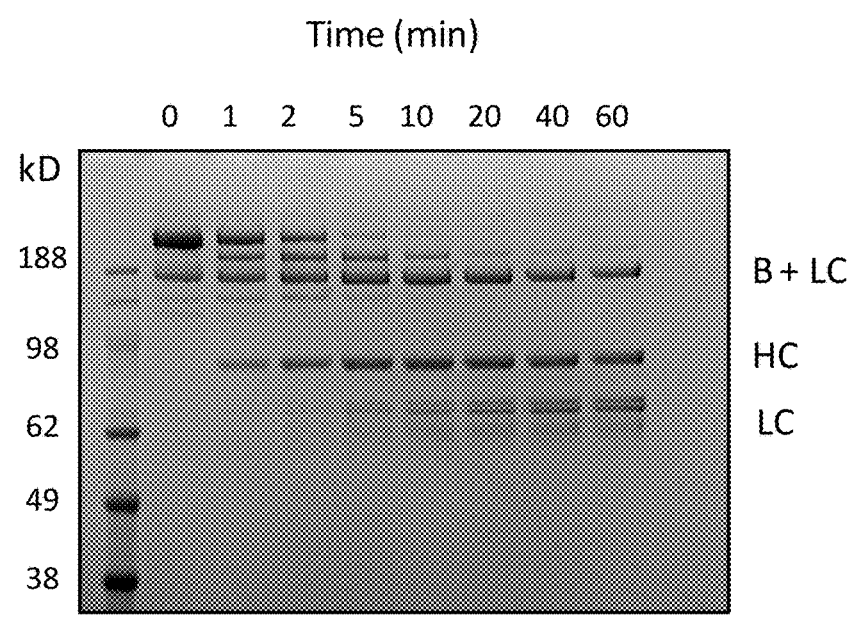

The FV basic peptide was also determined to delay proteolytic activation of FV by thrombin. In the absence of FVBR, thrombin rapidly cleaves Factor V at Arg709 to produce heavy chain (HC) and then rapidly cleaves at Arg1018 and Arg1545 to produce light chain (LC) (FIG. 4A). In the presence of FVBR, the cleavage at Arg709 proceeds normally (FIG. 4B). However, the presence of FVBR delayed cleavage at Arg1545 causes accumulation of B domain+light chain and reduces the amount of light chain.

Figure 5:
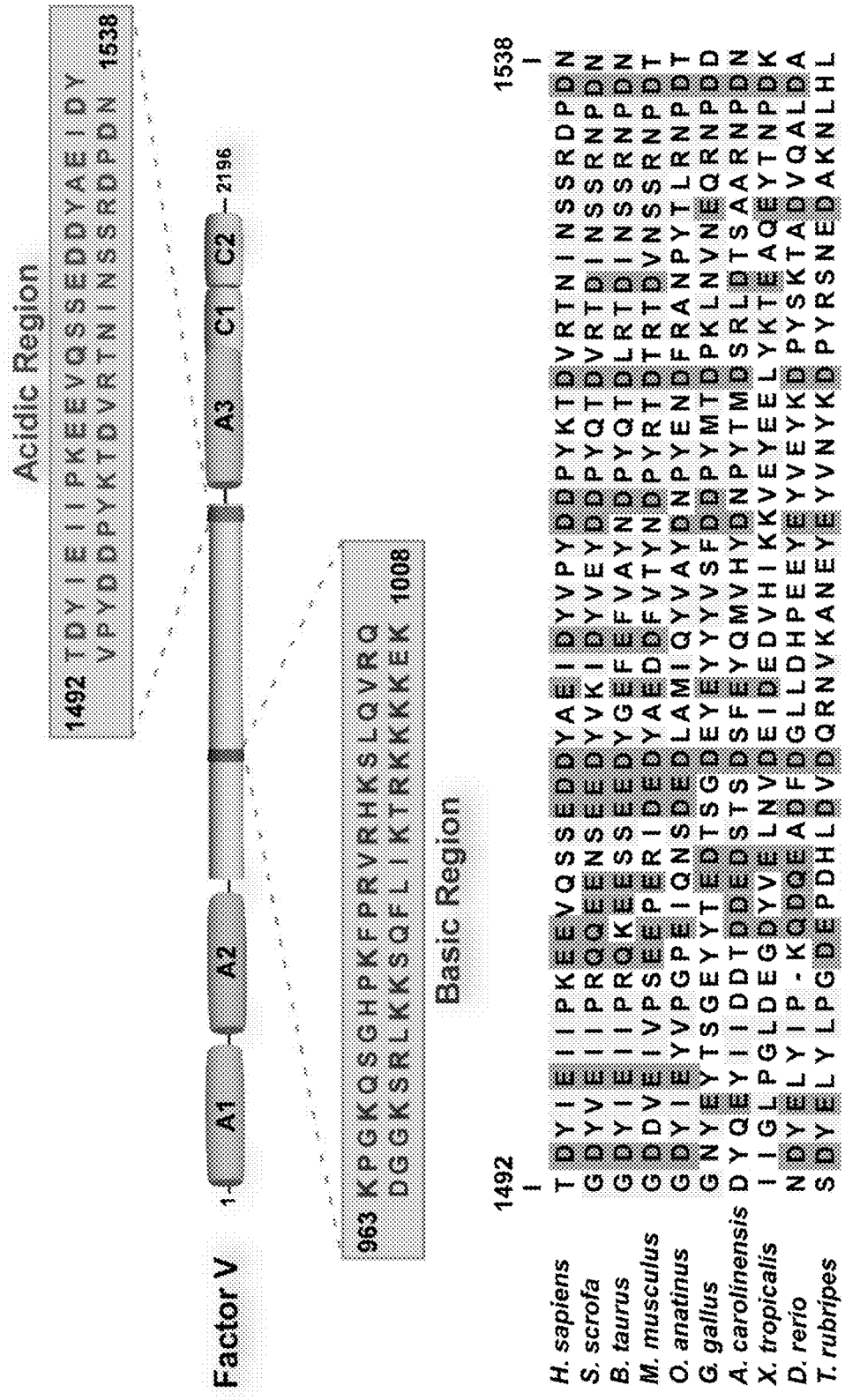
FIG. 5 provides a schematic of Factor V with the amino acid sequences of a conserved basic region (SEQ ID NO: 6) and a conserved acidic region (SEQ ID NO: 16) within the B domain. A sequence alignment of the conserved acidic region across various species is also provided. Sequences are SEQ ID NOs: 16-25, from top to bottom.
Figure 6:
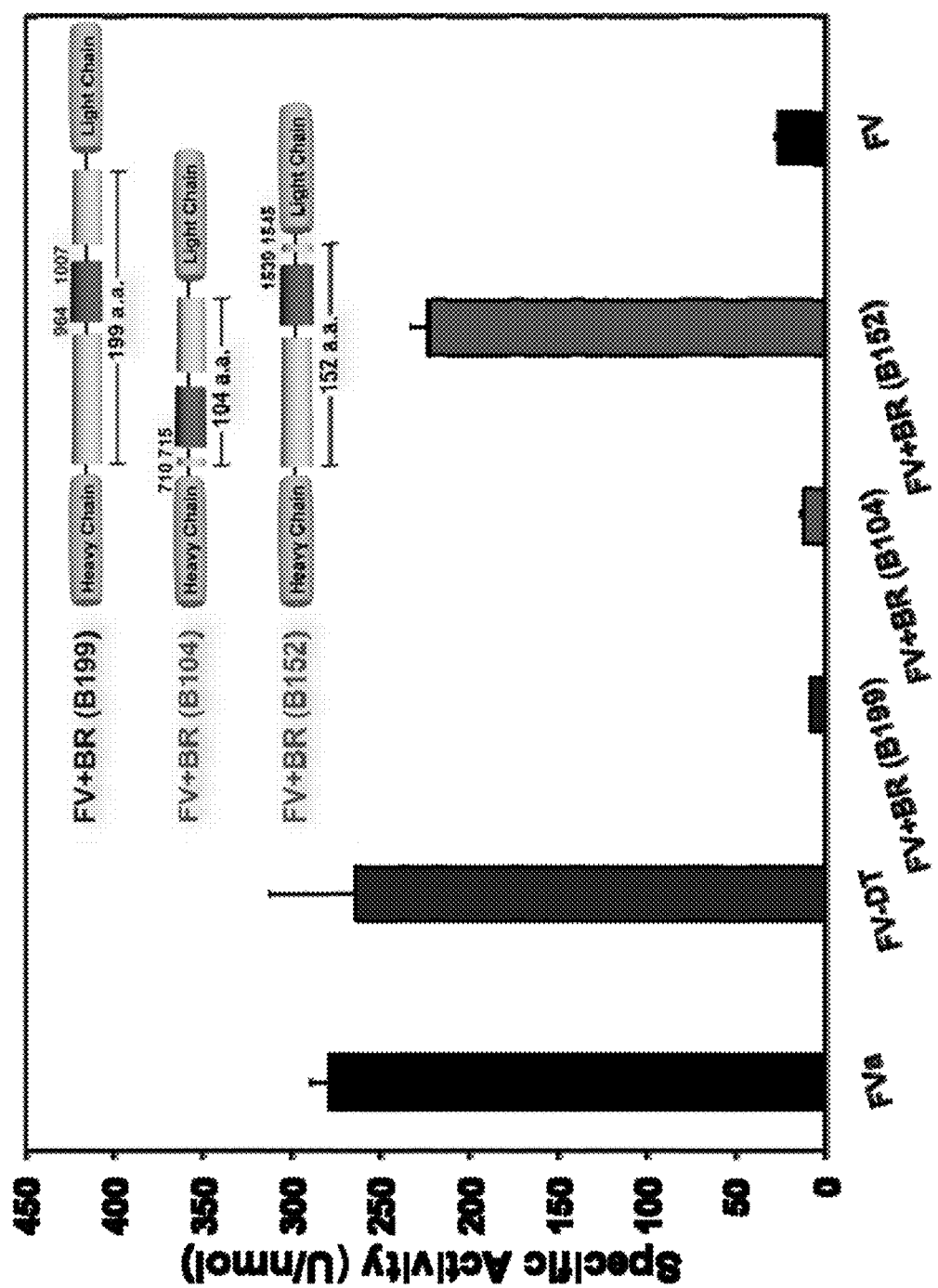
FIG. 6 provides a graph of the activity of various FV variants.

In addition to the conserved basic region, the Factor V B domain also has a conserved acidic region (FIG. 5). In order to determine if the Factor V acidic domain cooperates with the basic region to stabilize Factor V in an inactive state, a series of mutants were made. Specifically, B199, B104, and B152 were synthesized. B199 is a FV-DT variant in which amino acids 963-1008 were inserted between residues 810 and 1492; in B104, residues 716-810 from FV-DT were deleted and replaced with residues 963-1008; in B152, residues 1492-1538 of FV-DT were deleted and replaced with residues 963-1008. As seen in FIG. 6, the specific activity of B199 and B104 was dramatically reduced, but the activity of B152 approached the levels observed for FVa and FV-DT.

The data presented herein demonstrate that the basic region of the Factor V B domain functionally interacts with an acidic region in the B domain to stabilize Factor V in an inactive state. The mechanism of inhibition appears to be mediated at least in part by preventing and/or disrupting the binding of FXa with Factor V.

A Factor V basic region peptide effectively inhibits Factor V variants and slows the activation of Factor V by thrombin. These results indicate that the Factor V basic peptide can be used to regulate thrombin generation by limiting Factor V activation and cofactor activity.

Figures 7A, 7B:
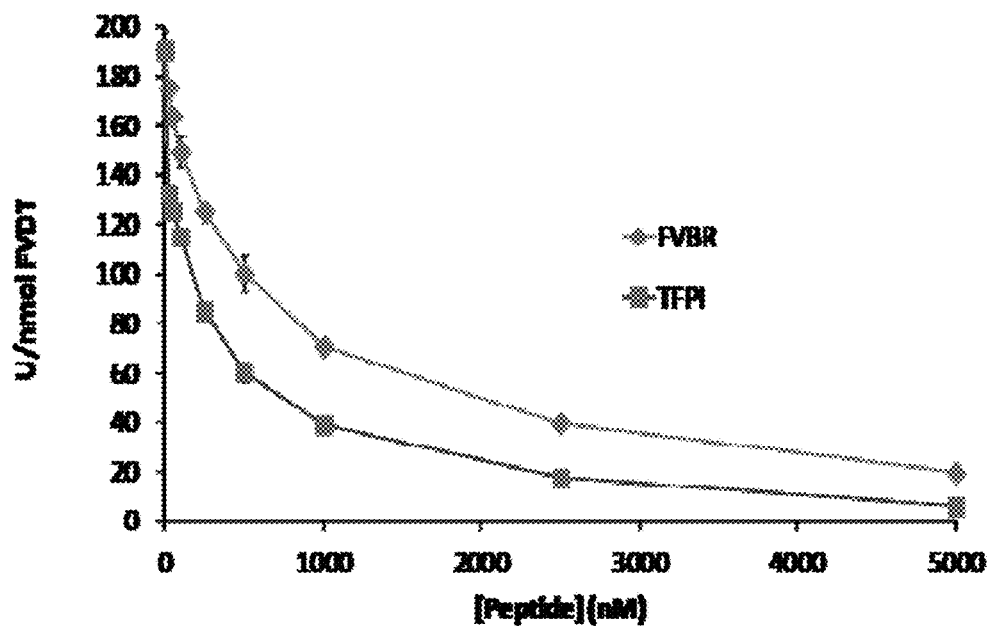
FIG. 7A shows a sequence alignment of the tissue factor pathway inhibitor (TFPI) C-terminal tail (SEQ ID NO: 4) and FVBR (SEQ ID NO: 2).
FIG. 7B provides a graph of the inhibition of FVDT by the FVBR or TFPI peptide.
Figure 7C:
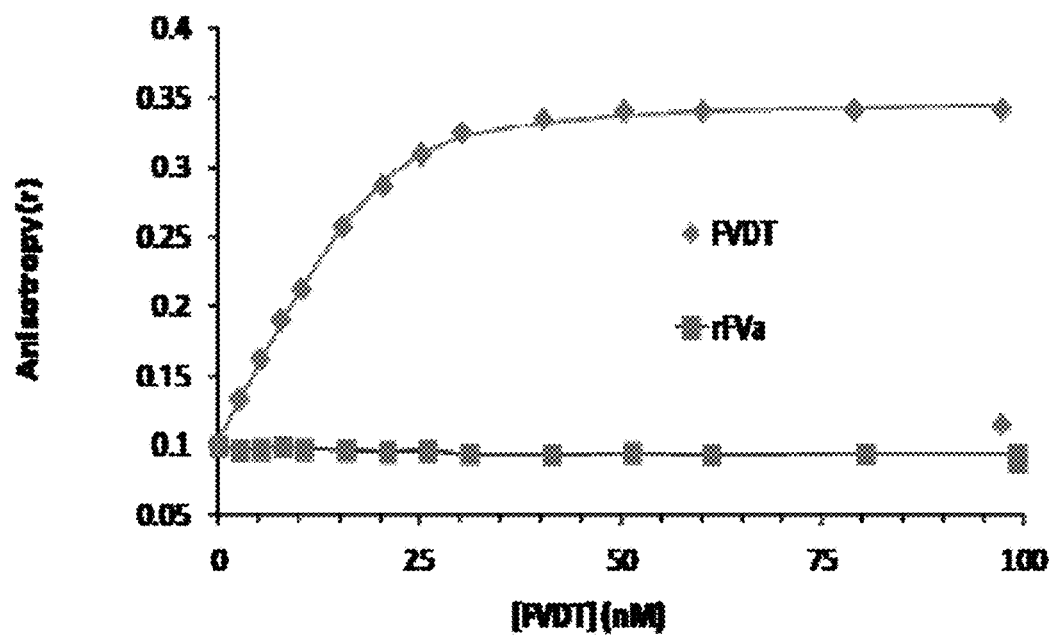
FIG. 7C shows the direct binding of TFPI to FVDT.
Figure 7D:
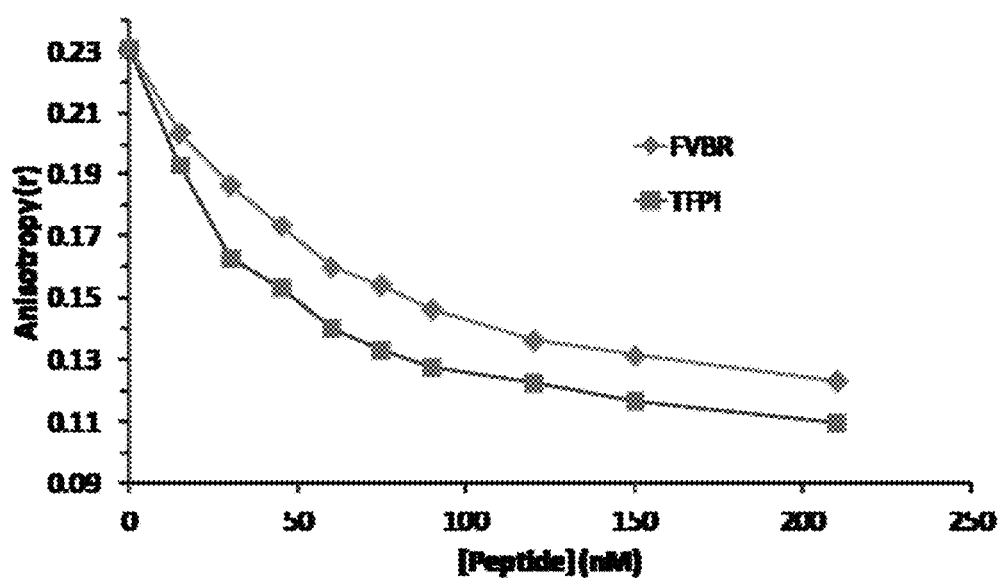
FIG. 7D shows a competition assay of unlabeled FVBR or TFPI with Oregon Green® 488 FVBR for binding with FVDT.
Figure 8A:
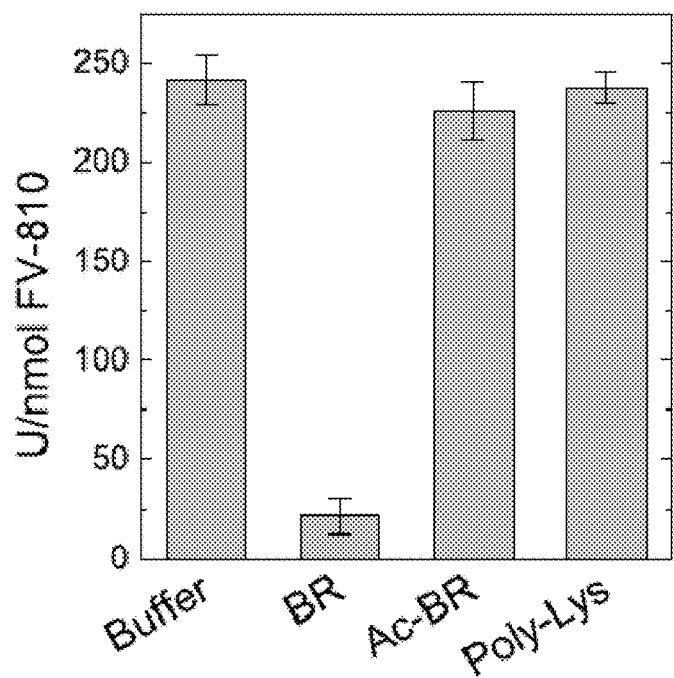
FIGS. 8A and 8B show the specific clotting activity measured in FV-deficient plasma supplemented with 0.25 nM FV-810 (FIG. 8A) or rFVa (FIG. 8B) and the indicated peptides at 5 µM. Ac-BR=acetylated BR peptide.
Figure 8B:
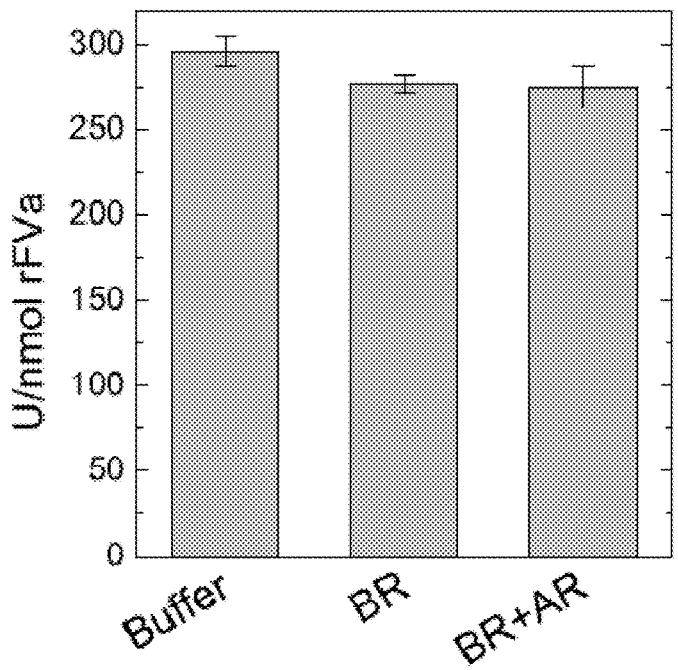

The C-terminal tail region of TFPI is homologous to FVBR. FIG. 7A provides a sequence alignment of FVBR and the C-terminus (amino acids 240-265) of tissue factor pathway inhibitor (TFPI). The TFPI peptide depicted in FIG. 7A was tested for it ability to inhibit FVDT. As seen in FIG. 7B, the TFPI peptide inhibited FVBT in a manner similar to FVBR. FIG. 7C shows that TFPI directly bound FVDT. FIG. 7D shows a competition assay of unlabeled FVBR or TFPI with Oregon Green® 488 labeled FVBR for FVDT.

EXAMPLE II

Experimental Procedures
Materials

The peptidyl substrate H-D-phenylalanyl-L-pipecolyl-L-arginyl-p-nitroanilide (S2238) was from Diapharma (West Chester, Ohio). Benzamidine, 4-amidinophenylmethanesulfonyl fluoride hydrochloride, isopropyl β-D-1-thiogalactopyranoside, BSA, and poly-L-lysine (average $M_r$=1000-5000) were from Sigma. Dansylarginine N-(3-ethyl-1,5-pentanediyl)amide (DAPA) was from Hematologic Technologies (Essex Junction, Vt.). All tissue culture reagents were from Invitrogen, except insulin/transferrin/sodium selenite was from Roche Applied Science. Small unilamellar phospholipid vesicles composed of 75% (w/w) hen egg L-α-phosphatidylcholine and 25% (w/w) porcine brain L-α-phosphatidylserine (PCPS; Avanti Polar Lipids, Alabaster, Ala.) were prepared and characterized as described (Higgins et al. (1983) J. Biol. Chem., 258:6503-6508).

Proteins

Human prothrombin, thrombin, FX, and FV were isolated from plasma and prepared as described (Baugh et al. (1996) J. Biol. Chem., 271:16126-16134; Buddai et al. (2002) J. Biol. Chem., 277:26689-26698; Katzmann et al. (1981) Proc. Natl. Acad. Sci., 78:162-166; Mann, K. G. (1976) Methods Enzymol., 45:123-156). Recombinant FX (rFX), rFXa, rFVa, plasma-derived FVa, FV-810 (FVDT), and the FV-810 variants FV-810$^{R709Q}$, FV-810$^{R1545Q}$, and FV-810$^{QQ}$ were prepared, purified, and characterized as described (Camire, R. M. (2002) J. Biol. Chem., 277:37863-37870; Toso et al. (2008) J. Biol. Chem., 283:18627-18635; Toso et al. (2004) J. Biol. Chem., 279:21643-21650). Prethrombin-2 was prepared by proteolysis of human prothrombin and purified as described (Mann et al. (1981) Methods Enzymol., 80:286-302). Molecular weights and extinction coefficients ($E_{0.1\%}$=280 nm) of the various proteins have been reported (Zhu et al. (2007) J. Biol. Chem., 282:15033-15039). All functional assays were performed at 25° C. in assay buffer (20 mM HEPES, 150 mM NaCl, 5 mM CaCl$_2$, and 0.1% polyethylene glycol 8000, pH 7.5).

Construction of FV B-Domain Peptides

BR cDNA-encoding residues Ser$^{951}$-Lys$^{1008}$ of FV was amplified from FV cDNA using primers A (5'-GCAAGGTCTCAAGGTTCACGTGCTTGGGGA-GAAAGCACC-3', forward; SEQ ID NO: 26) and B (5'-GCTTGTCGACTTACTTCTCTTTTTTCTTTT TTCGTGTCTTAATGAGAAACTGG-3', reverse; SEQ ID NO: 27). The BR+AR peptide (968-1007 and 1492-1538), encoding the juxtaposed BR and AR sequences from the FV variant FVB104, was amplified from FV-B104 cDNA using primers C (5'-GCAAGGTCTCAAGG TAGTGGCCAC-CCAAAGTTTCCTAGAG-3', forward; SEQ ID NO: 28) and D (5'-GCTTGTCGACTTAGTTGTCAGGATCTCTG-GAGGAGTTGA TGTTTGTCC-3', reverse; SEQ ID NO: 29). Bovine BR (*Bos taurus* Ser$^{938}$-Lys$^{996}$), green anole BR (*Anolis carolinensis* Ser$^{1331}$-Lys$^{1393}$), and zebrafish BR (*Danio rerio* Ser$^{1260}$-Lys$^{1318}$) cDNAs were synthesized by GenScript (Piscataway, N.J.). Amplified cDNAs were digested with the restriction enzymes BsaI (5') and SalI (3') and ligated into the pE-SUMO bacterial expression vector (LifeSensors, Malvern, Pa.), which had been digested with the same restriction enzymes. All constructs were verified by DNA sequencing.

Expression and Purification of B-Domain Peptides

Sequence-verified bacterial expression constructs were transformed into chemically competent BL21 (DE3) cells (EMD Millipore, Billerica, Mass.), and single colonies were used to inoculate liquid LB cultures containing 50 µg/ml kanamycin (LB-Kan$_{50}$). Starter cultures were subcultured into 1 liter of LB-Kan$_{50}$ and incubated at 37° C. until A$_{600}$ reached 0.5, at which point, isopropyl β-D-1-thiogalactopyranoside was added at a final concentration of 1 mM. After 2 hours, cells were pelleted, resuspended in lysis buffer (20 mM Tris, 150 mM NaCl, and 1% Triton X-100, pH 8), and lysed with a Misonix Sonicator® 3000 system (Qsonica, Newtown, Conn.). Cell debris was pelleted, and the small ubiquitin-like modifier (SUMO) fusion proteins were purified on HisTrap™ FF columns (GE Healthcare) following the manufacturer's instructions. Purified SUMO fusion proteins were incubated with SUMO protease (LifeSensors) for 2 hours at 30° C. to remove the SUMO fusion, and cleaved peptides were purified by cation exchange chromatography. Protein purity was assessed by SDS-PAGE using 4-12% gradient gels (Invitrogen) in MES buffer, followed by staining with Coomassie Brilliant Blue R-250.

Peptide Acetylation and Fluorescent Labeling

The BR peptide was acetylated by incubation with a 20-fold molar excess (relative to amine groups) of N-hydroxysulfosuccinimide acetate (Thermo Scientific) for 1 hour at 25° C. in 20 mM HEPES, 150 mM NaCl, 2 mM CaCl$_2$, and pH 7.4. Mass spectroscopy data of the acetylated BR peptide were consistent with quantitative modification of all Lys residues and the N terminus. Fluorescent labeling of the BR peptide was performed by incubating the BR peptide containing an N-terminal Cys (Cys-BR) for 10 min at 25° C. with a 10-fold molar excess of tris(2-carboxyethyl)phosphine HCl (Thermo Scientific) to reduce disulfide bonds, followed by 2 hours at 25° C. with a 20-fold molar excess of either Oregon Green® 488 maleimide or QSY7 C5-maleimide (Invitrogen). The reactions were quenched by the addition of excess DTT, and labeled BR peptides were purified by gel filtration through Bio-Gel® P-6DG resin (Bio-Rad) to remove excess labeling reagents.

Prothrombin and Prethrombin-2 Activation Assays

Steady-state initial velocities of prothrombin cleavage were determined discontinuously at 25° C. as described (Camire, R. M. (2002) J. Biol. Chem., 277:37863-37870). Reaction mixtures containing PCPS (50 μM), DAPA (3 μM), prothrombin (1.4 μM), and either rFVa or the indicated FV-810 derivatives were incubated with B-domain peptides (0-10 μM) in assay buffer. Reactions were initiated with FXa (2 nM), and aliquots were quenched in buffer containing 50 mM EDTA at multiple time points. Prothrombin activation was determined using the chromogenic thrombin substrate 52238 as described (Camire, R. M. (2002) J. Biol. Chem., 277:37863-37870). Prethrombin-2 activation was measured similarly to prothrombin using the following reaction conditions: 50 μM PCPS, 1.4 μM prethrombin-2, 3 μM DAPA, 5 nM rFVa or FV-810 derivatives, 1-50 nM FXa, and 0-1000 nM BR peptide.

Clotting Assays

FV derivatives (500 nM) were prepared in assay buffer. Where noted, FV derivatives were pretreated with 10 nM thrombin for 15 minutes at 37° C., followed by the addition of 15 nM hirudin. Samples were diluted to 0.25 nM in assay buffer with 0.1% BSA, and the specific clotting activity was measured in FV-deficient plasma (George King Bio-Medical, Overland Park, Kans.) with TriniCLOT PT Excel (Tcoag, Wicklow, Ireland) as described (Camire et al. (1998) Biochemistry 37:11896-11906). The data are presented as the means±S.D.

Fluorescence Anisotropy Measurements

Steady-state fluorescence anisotropy was measured at 25° C. in a PTI Quanta-Master™ fluorescence spectrophotometer (Photon Technology International, Birmingham, N.J.) using excitation and emission wavelengths of 480 and 520 nm, respectively, with long-pass filters (KV500, CVI Melles Griot) in the emission beam. Reaction mixtures (2.5 ml) containing fixed concentrations (20-40 nM as indicated) of Oregon Green® 488 maleimide-modified BR (OG488-BR) and 50 μM PCPS in assay buffer were prepared in 1-$cm^2$ quartz cuvettes to which increasing concentrations of FVa or FV-810 were added. Fluorescence anisotropy measurements, including controls, were performed as described (Buddai et al. (2002) J. Biol. Chem., 277:26689-26698; Betz et al. (1998) J. Biol. Chem., 273:10709-10718).

Analytical Ultracentrifugation

Analytical ultracentrifugation of QSY7 C5-maleimide-modified BR (QSY7-BR) was performed in a Beckman Optima XL-I analytical ultracentrifuge using absorbance optics. Sedimentation velocity was measured at 25,000 or 45,000 rpm with two-sector cells in an An-60 Ti rotor at 20° C. Sedimentation of QSY7-BR was followed measuring absorbance at 560 nm in cells containing 5 μM QSY7-BR alone or with 7 μM FV-810 or rFVa in 20 mM HEPES, 150 mM NaCl, and 2 mM $CaCl_2$, pH 7.4. Sedimentation coefficients and molecular weights were determined by g(s*) analysis performed using DCDT+ (Philo, J. S. (2000) Anal. Biochem., 279:151-163).

Data Analysis

Data were analyzed by nonlinear least squares regression analysis using the Marquardt algorithm (Bevington et al. (1992) *Data Reduction and Error Analysis for the Physical Sciences*, pp. 141-167, McGraw-Hill, New York), and the quality of each fit was assessed as described (Straume et al. (1992) Methods Enzymol., 210:87-105). Equilibrium dissociation constants ($K_d$) and stoichiometries (n) for the interaction between OG488-BR and FV-810 in saturation binding measurements were obtained from the change in OG488-BR anisotropy over increasing concentrations of FV-810, which was corrected for the overall change in fluorescence intensity (Buddai et al. (2010) J. Biol. Chem. 285:5212-5223; Krishnaswamy, S. (1990) J. Biol. Chem., 265:3708-3718). Displacement binding experiments, in which unlabeled BR or FXaS195A were titrated into preformed complexes of OG488-BR FV-810, were analyzed to determine $K_d$ and n as described (Betz et al. (1998) J. Biol. Chem., 273:10709-10718). In prothrombin-2 activation reactions, $K_d$ values for the interactions of BR and FXa with FV-810 were obtained by global analysis of prethrombin-2 activation rates at varying concentrations of FXa and BR fit to a model of tight binding using DYNAFIT (Kuzmic, P. (1996) Anal. Biochem., 237:260-273).

Results

Figure 9:
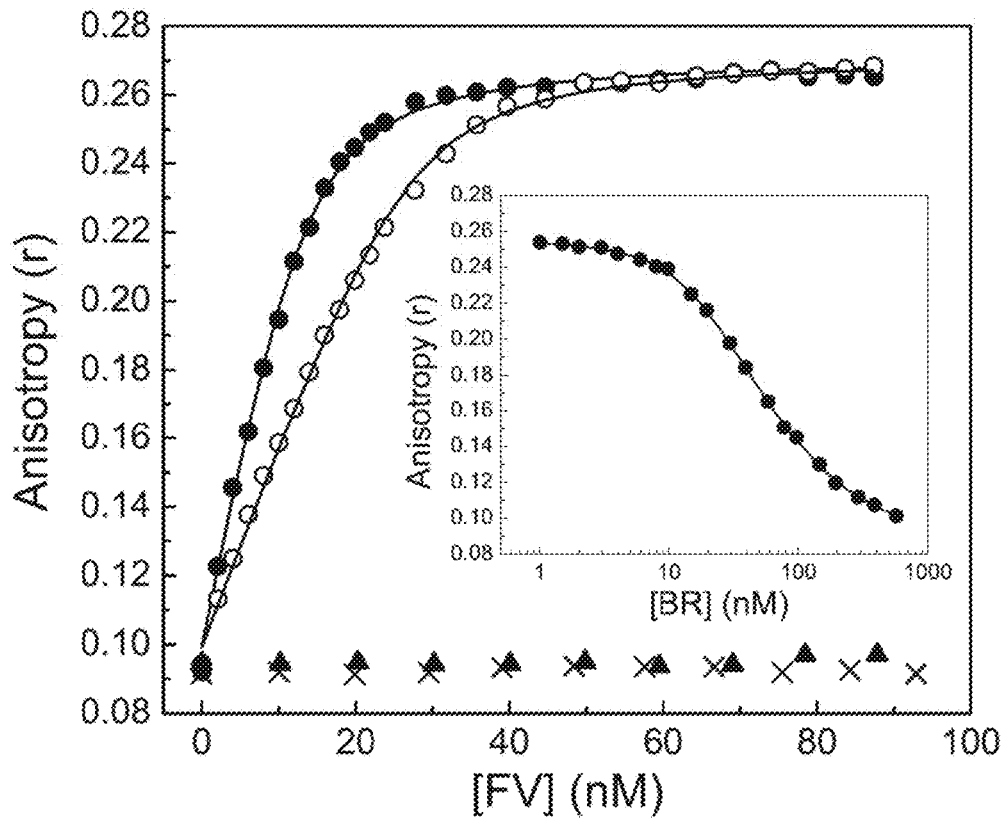
FIG. 9 shows the direct binding of the BR peptide to FV-810. FV-810 was titrated into reaction mixtures containing 20 nM (●) or 40 nM (○) OG488-BR peptide and 50 µM PCPS in assay buffer at 25° C. Lines were drawn after analysis to independent, non-interacting sites with the fitted constants Kd=2.07±0.2 nM and n=1.27±0.02 mol of FV-810/mol of OG488-BR at saturation. Control experiments were performed by titrating FV-810 into buffer containing 10 mM EDTA (X) or by titrating rFVa (▲). Inset, the unlabeled BR peptide was titrated into reaction mixtures containing 30 nM OG488-BR, 20 nM FV-810, and 50 µM PCPS. The fitted constants for the unlabeled BR peptide were determined as Kd=2.1±0.2 nM and n=1.0±0.06 mol of BR/mol of FV-810 assuming the constants determined above for OG488-BR.

Inhibition of Cofactor-Like FV Variants by B-Domain Fragments

As explained hereinabove, a minimal inhibitory motif has been identified within the FV B-domain that consists of evolutionarily conserved basic and acidic elements. To define how these elements inhibit FV function, B-domain fragments were expressed as SUMO fusions in *Escherichia coli* and purified by ion exchange chromatography following removal of the SUMO tag. As explained hereinabove, the inhibitory effects of the purified fragments were determined in assays containing either FVa or the cofactor-like FV variant FV-810. In reconstituted prothrombin activation reactions, the BR peptide effectively inhibited prothrombinase containing FV-810 (see above). The clotting activity of FV-deficient plasma supplemented with FV-810 was similarly inhibited in the presence of the BR peptide (FIGS. 2D and 8), indicating that the BR peptide reconstituted a functional inhibitory procofactor regulatory region (PRR) within FV-810. In contrast to FV-810, the BR peptide had no inhibitory effect on rFVa in prothrombin activation assays or clotting assays (FIGS. 2 and 8). Furthermore, whereas a minimal B-domain almost exclusively composed of tandem BR and AR elements is sufficient to stabilize FV as a procofactor, rFVa was not inhibited by the BR+AR peptide (FIG. 8B). Thus, whereas the BR can act in trans to reconstitute the PRR, it appears that the acidic region (AR) must be covalently attached to mediate inhibition of procoagulant activity.

The complementary charge states of the BR and AR elements suggest the electrostatic forces likely contribute to PRR function. Indeed, the BR peptide that had been acetylated to neutralize the positive charge no longer inhibited FV-810 (FIG. 8A). However, positive charge alone was insufficient to reconstitute a functional PRR, as neither low molecular weight poly-L-lysine (average $M_r$=1000-5000) (FIG. 8A) nor the cationic platelet factor 4 affected FV-810 activity. Thus, inhibition of FV by the PRR is both charge- and sequence-dependent.

Direct Binding of the BR Peptide to FV Variants

The ability of the BR peptide to inhibit FV-810 suggests that the peptide binds to FV-810 to reconstitute a functional PRR. To test this, direct binding of the BR peptide to FV-810 or rFV was measured using multiple approaches. First, the BR peptide was fluorescently labeled with Oregon Green® 488 maleimide, and changes in fluorescence anisotropy were monitored. Titration of FV-810 into reactions containing fixed concentrations of OG488-BR produced saturable binding curves (FIG. 9) with calculated equilibrium binding values of $K_d=2.07\pm0.2$ nM and n=1.27±0.02 mol of FV-810/mol of OG488-BR. The binding of OG488-BR to FV-810 was calcium-dependent, as no binding was observed when 10 mM EDTA was added to the buffer. Titrating the unlabeled BR peptide into reactions containing a preformed complex of OG488-BR and FV-810 reduced the anisotropy signal toward the base line (FIG. 9, inset). From these displacement curves, the equilibrium binding values for the unlabeled BR peptide were calculated to be $K_d=2.1\pm0.2$ nM and n=1.0±0.06 mol of BR/mol of FV-810, essentially identical to the labeled peptide. In contrast to FV-810, rFVa showed no detectable binding to OG488-BR (FIG. 9).

Figure 10A:
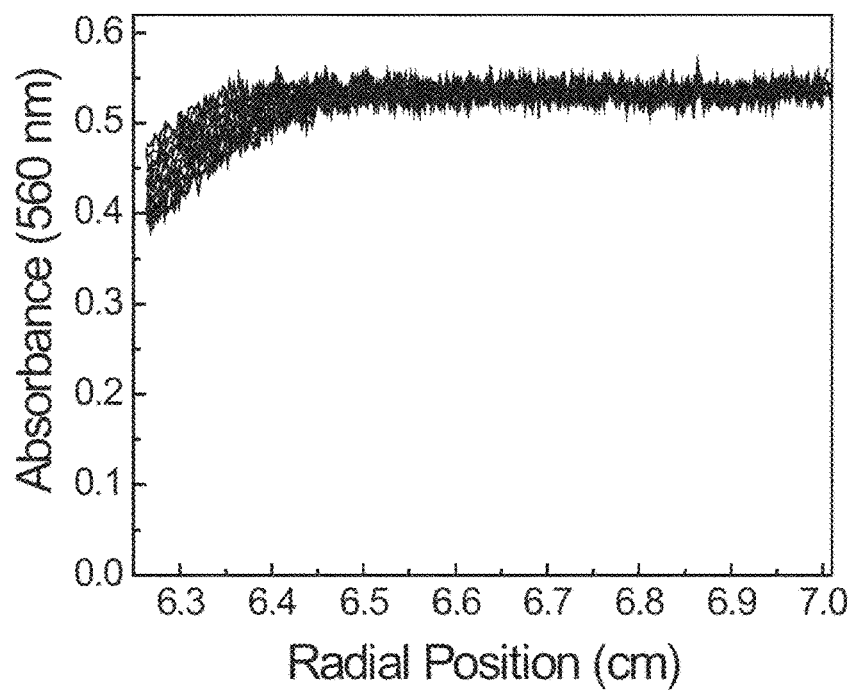
FIGS. 10A and 10B show sedimentation velocity of the BR peptide. The sedimentation velocity of 5 µM QSY7-BR was measured either alone (FIG. 10A) or in the presence of 7 µM FV-810 (FIG. 10B). The panels show 14 scans taken at 8-minute intervals.
Figure 10B:
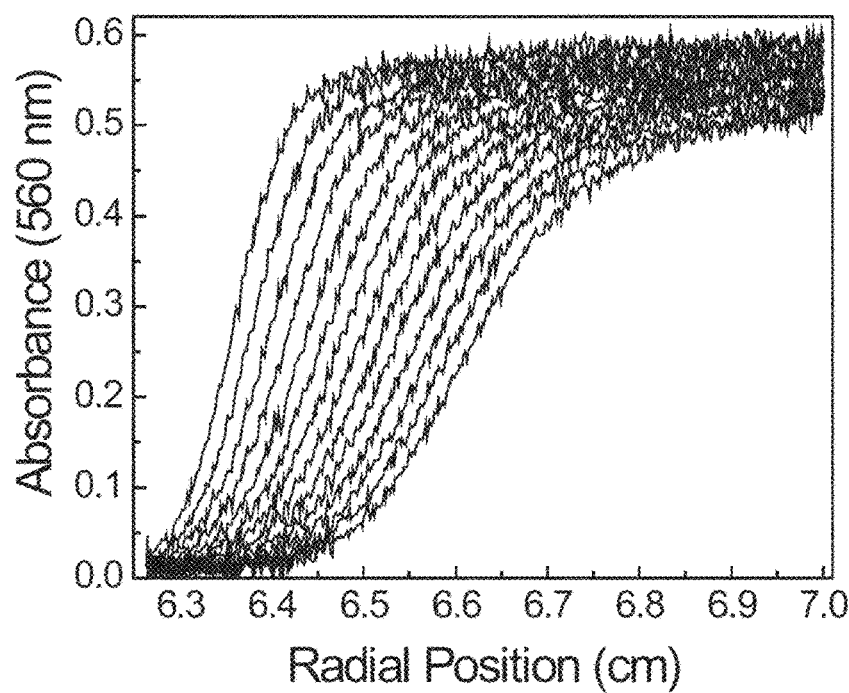
Figure 11B:
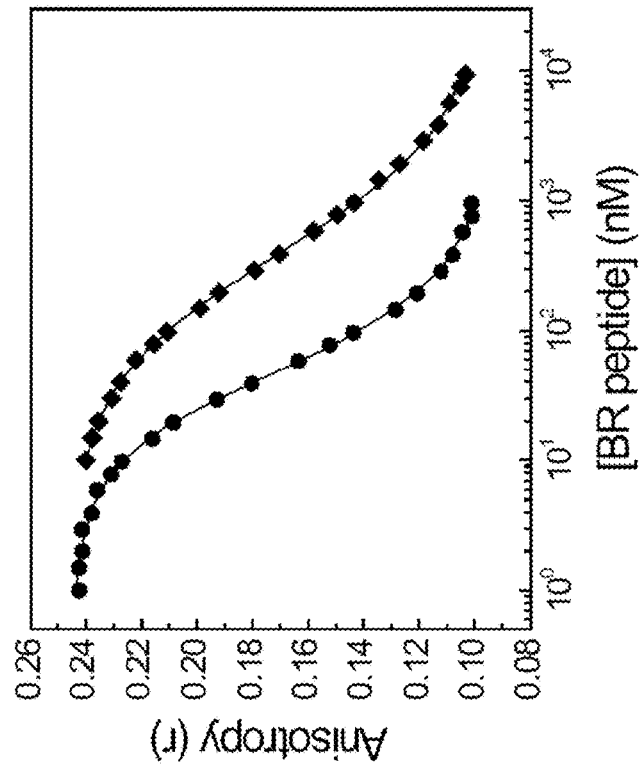
FIG. 11B shows human (●) and bovine (♦) BR peptides titrated into reactions containing 30 nM OG488-BR, 20 nM FV-810, and 50 µM PCPS at 25° C. Fluorescence anisotropy was measured, and equilibrium binding constants were determined assuming a stoichiometry of 1 mol of FV-810/mol of BR peptide: the human BR, Kd=2.2±0.2 nM; and the bovine BR, Kd=28.3±0.6 nM.
Figure 11A:
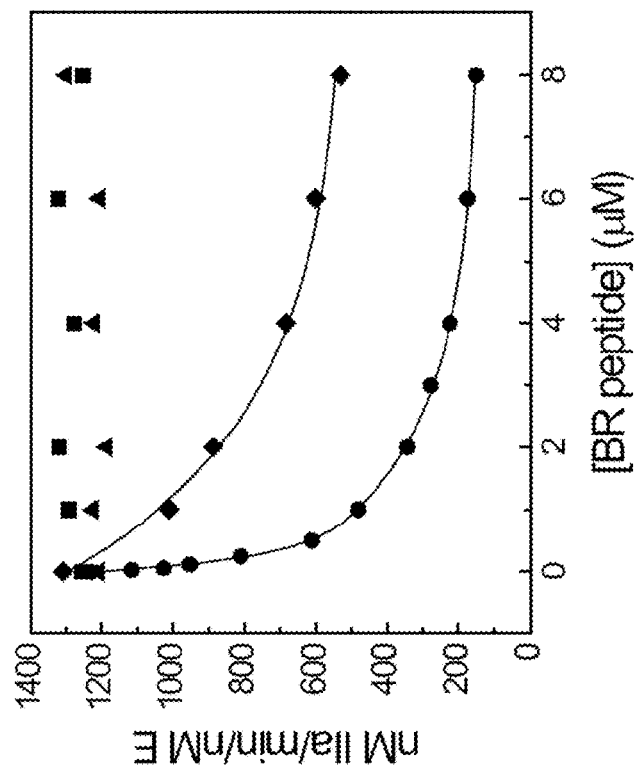
FIG. 11A shows human (●), bovine (♦), lizard (▲), and zebrafish (■) BR peptides titrated into reactions containing 1.4 µM prothrombin, 3 µM DAPA, 50 µM PCPS, and 0.1 nM FV-810 in assay buffer at 25° C. Prothrombin activation was measured.
Figure 12A:
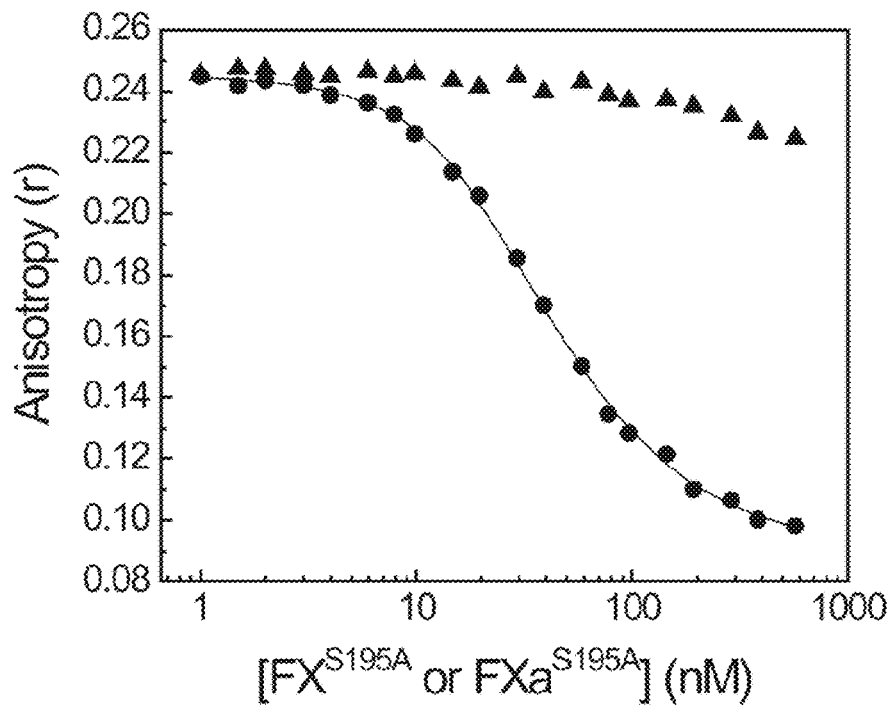
FIGS. 12A and 12B show the competitive binding of the BR peptide and FXa to FV-810.
Figure 12B:
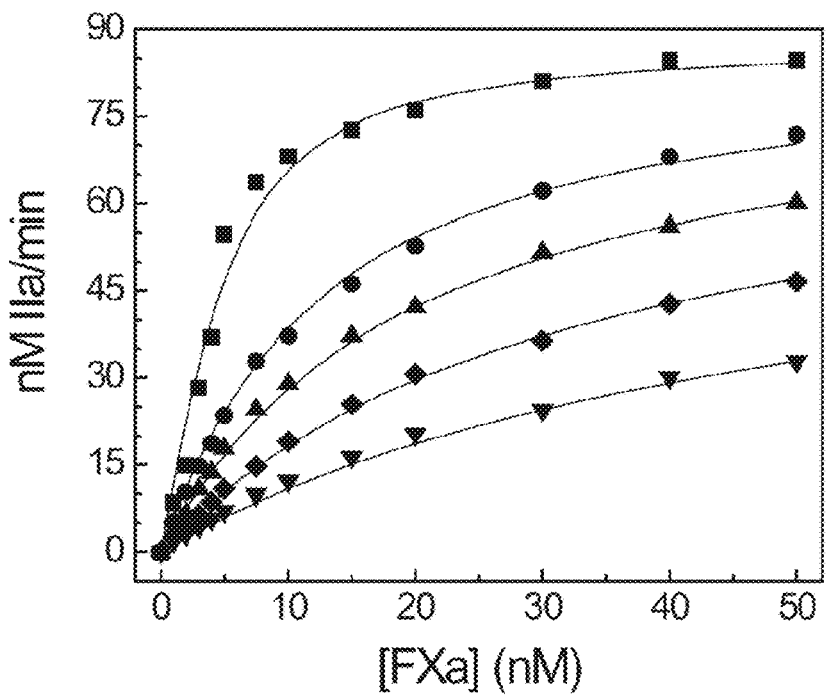
Figure 13:
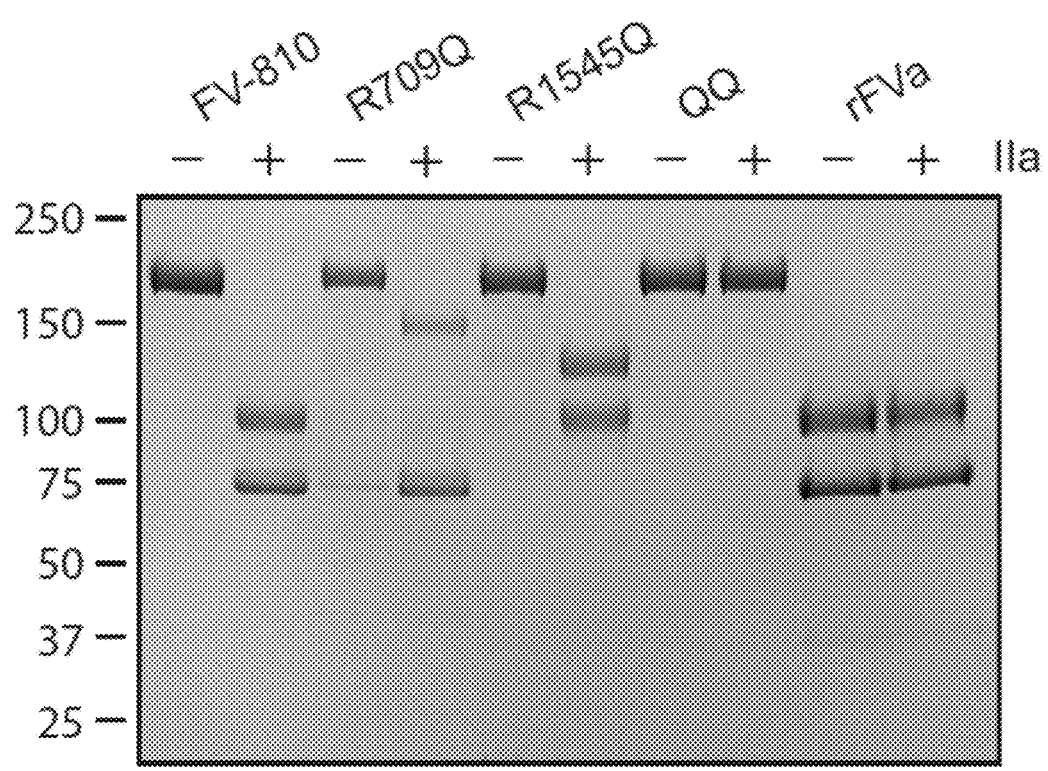
FIG. 13 provides an image of a gel of reactions containing 600 nM FV-810, FV-810$^{R709Q}$, FV-810$^{R1545Q}$, FV-810$^{QQ}$, or rFVa incubated for 15 min at 37° C. with buffer or 10 nM thrombin and then quenched with 20 nM hirudin. Samples were resolved by 4-12% gradient SDS-PAGE under reducing conditions and stained with Coomassie Brilliant Blue.
Figure 14A:
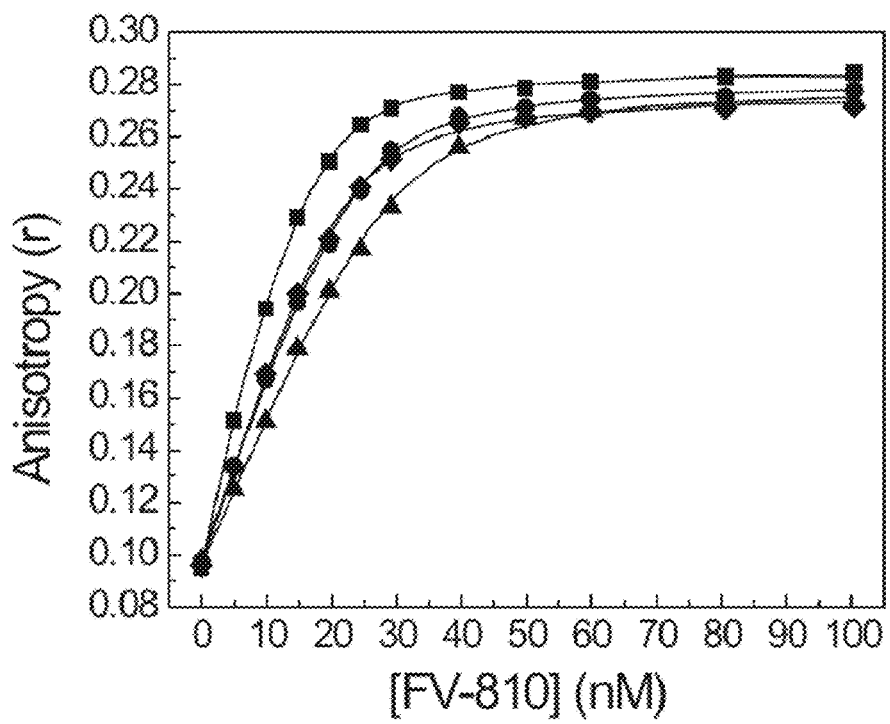
FIGS. 14A and 14B show the direct binding of OG488-BR to thrombin-cleaved FV-810 variants. FV-810 (●), FV-810$^{R709Q}$ (▲), FV-810$^{R1545Q}$ (♦), and FV-810$^{QQ}$ (■) were pretreated with buffer (FIG. 14A) or thrombin (FIG. 14B). Quenched FV-810 species were titrated into reaction mixtures containing 30 nM OG488-BR and 50 µM PCPS in assay buffer, and changes in the fluorescence anisotropy signal were measured. Binding constants were calculated assuming a stoichiometry of n=1 of mol FV-810/mol of OG488-BR: FV-810, Kd=2.1±0.3 nM; FV-810$^{R709Q}$, Kd=7.1±1.6 nM; FV-810$^{R1545Q}$, Kd=2.0±0.4 nM; and FV-810$^{QQ}$, Kd=0.31±0.29 nM. After incubation with thrombin, neither FV-810 nor FV-810$^{R709Q}$ had detectable binding to OG488-BR, whereas FV-810$^{QQ}$ bound with a calculated Kd of 1.3±0.1 nM, and FV-810$^{R1545Q}$ bound with a Kd of 30.3±4.1 nM.
Figure 14B:
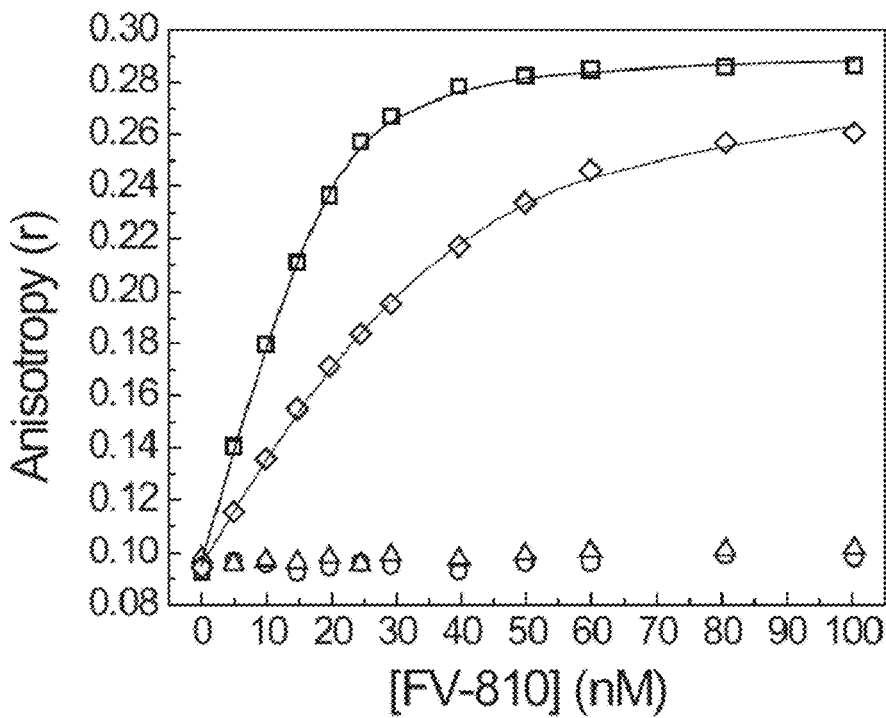

As a complementary approach, binding between the BR peptide and FV-810 was also monitored by analytical ultracentrifugation. Sedimentation velocity experiments were performed with 5 µM QSY7-BR either alone (FIG. 10A) or with 7 µM FV-810 (FIG. 10B). In the absence of FV-810, the sedimentation coefficient ($s^0_{20,w}$) of QSY7-BR was 0.98 s, identical to the value for recombinant hirudin, which is similar in size (Otto et al. (1991) Eur. J. Biochem., 202:67-73). In the presence of FV-810, the QSY7-BR sedimentation coefficient shifted to 9.8 s, somewhat larger than the determined value for FV-810 of 8.43 s (Toso et al. (2004) J. Biol. Chem., 279:21643-21650). This increase in the sedimentation coefficient is consistent with a 1:1 stoichiometry between QSY7-BR and FV-810, agreeing with the calculated stoichiometry from fluorescence measurements. Molecular weight determination yielded Mr=7210±40 for the QSY7-labeled peptide and Mr=199,000±3000 for QSY7-BR-FV-810 complex, which are in agreement with expected values. QSY7-BR sedimentation velocity was also performed with rFVa or with FV-810 in buffer containing 10 mM EDTA as controls. The data from these control experiments indicated a weak interaction ($K_d\geq1$ µM) consistent with the anisotropy data showing that no detectable binding was observed using ≤100 nM FVa (FIG. 9).

PRR Sequence Specificity

To assess the sequence specificity of the PRR, BR fragments were generated from several vertebrate species and their effect on FV-810 was compared with that of the human BR. The bovine BR, which is highly conserved with the human BR (FIG. 1), inhibited FV-810 in both prothrombin activation reactions and clotting assays compared with the human BR, whereas the more divergent BR fragments from lizard (*A. carolinensis*) and zebrafish (*D. rerio*) had no effect on FV-810 activity (FIG. 11A). In displacement binding experiments, the bovine BR exhibited ~10-fold weaker binding to FV-810 than did the human BR ($K_d$=28.3±0.6 versus 2.2±0.2 nM, respectively) (FIG. 11B).

Competition Between the BR and FXa

A fundamental difference between procofactor-like and cofactor-like FV proteins is the ability of the latter to bind to FXa with high affinity. As demonstrated herein, a minimal B-domain consisting almost exclusively of the PRR is sufficient to maintain the procofactor state. The PRR likely occludes a high affinity FXa-binding site on FV; thus, inhibition of FV-810 procoagulant function by the BR peptide could reflect competitive binding between the BR and FXa to FV(a). Consistent with this, when catalytically inactive FXaS195A was titrated into fluorescence binding assays, it displaced OG488-BR from FV-810 (FIG. 12A). Using the previously determined binding constants for OG488-BR, it was calculated that $FXa^{S195A}$ bound to FV-810 with $K_d$=1.8 nM and n=1.1 mol FXa/mol of FV-810, consistent with the reported equilibrium binding values for FXa and FV-810 (Toso et al. (2004) J. Biol. Chem., 279: 21643-21650). As a control, titration of zymogen FXS195A at concentrations up to 1 μM had little effect on OG488-BR anisotropy (FIG. 12A).

The competition between the BR peptide and FXa was also assessed by monitoring prethrombin-2 activation in reactions containing variable concentrations of FXa and the BR peptide at a fixed concentration of FV-810. Under these reaction conditions, the BR and FXa followed a model of competitive binding (FIG. 12B), with fitted equilibrium binding values $K_d$=2.0±0.2 nM for FXa and $K_d$=34.2±3.6 nM for the BR. The calculated $K_d$ for the BR from these reactions is somewhat higher than that observed in direct binding measurements (FIG. 9). This discrepancy may be due to the generation of FVa in the reactions from feedback proteolysis of FV-810 by thrombin. Together with the fluorescence binding data, these results indicate a model of competitive binding of the BR and FXa to FV-810.

Role of Site-Specific Proteolysis in PRR Stability and Inhibition

The observation that rFVa activity is not inhibited by any of the B-domain peptides suggests that proteolysis of the FV B-domain by thrombin irreversibly disrupts the PRR, thereby producing the active cofactor FVa. The effect of proteolysis was assessed at individual thrombin cleavage sites on PRR function by comparing the ability of the BR peptide to inhibit FV-810 cleaved by thrombin at either Arg709 or Arg1545. FV-810 variants containing the R709Q or R1545Q mutation were preincubated with thrombin to generate cleavage products in which the B-domain was still tethered to either the heavy and/or light chains (FIGS. 2C and 13). Prior to thrombin cleavage, all FV-810 variants were potently inhibited by the basic peptide (FIGS. 2C and 13). However, following incubation with thrombin, only $FV\text{-}810^{R1545Q}$ and $FV\text{-}810^{QQ}$ were still inhibited by the BR peptide (FIGS. 2C and 13). Furthermore, when binding of the thrombin-cleaved FV-810 variants to OG488-BR was measured by fluorescence anisotropy, only $FV\text{-}810^{R1545Q}$ and $FV\text{-}810^{QQ}$ still bound OG488-BR, whereas FV-810 and $FV\text{-}810^{R709Q}$ did not (FIG. 14). Thus, cleavage of FV at Arg1545 specifically disrupts the ability of the BR to bind to FV-810 and establish a functional PRR. Interestingly, cleavage at Arg709 appears to partially destabilize the PRR, as $FV\text{-}810^{R1545Q}$ displayed a weakened binding affinity for OG488-BR after thrombin cleavage ($K_d$=30 versus 2 nM). This observation indicates that proteolytic activation of FV progressively disrupts the structural integrity of the PRR, thereby reducing its inhibitory effect.

In summary, the data presented herein provide mechanistic insight to explain how the B-domain stabilizes FV as an inactive procofactor and how discrete proteolysis of FV generates an active cofactor for FXa. The bipartite PRR, composed of cis- and trans-acting acidic and basic elements, respectively, suppresses cofactor activity by competitively inhibiting FXa binding to FV. Discrete proteolysis of the B-domain by thrombin destabilizes the PRR, with cleavage of the $Arg^{1545}$ peptide bond causing irreversible dissolution of PRR integrity and fully exposing a high affinity FXa-binding site. The ability of the BR to function as a trans-acting inhibitor of FV(a) activity offers a novel target for modulating FV(a) activity in vivo. Specifically, ligands that mimic the BR will function as anticoagulants by opposing or delaying full FV activation in the early stages of coagulation.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An isolated peptide selected from the group consisting of:
   i) a peptide having at least 80% homology with SEQ ID NO: 1, 2, or 3, wherein said peptide has a length of about 20 to about 80 amino acids and
   ii) a peptide consisting of SEQ ID NO: 4.

2. The isolated peptide of claim 1, wherein said peptide has at least 90% homology with SEQ ID NO: 1, 2, or 3.

3. The isolated peptide of claim 1, wherein said peptide comprises SEQ ID NO: 1, 2, or 3.

4. The isolated peptide of claim 1, wherein said peptide comprises SEQ ID NO: 3.

5. The isolated peptide of claim 1, wherein said peptide comprises at least one modification selected from the group consisting of amidation and acetylation.

6. A composition comprising at least one peptide of claim 1 and at least one pharmaceutically acceptable carrier.

7. The composition of claim 6, further comprising at least one anti-thrombosis compound.

8. The isolated peptide of claim 1, wherein said peptide has a length of about 20 to about 60 amino acids.

9. The isolated peptide of claim 1, wherein said peptide comprises at least one D-amino acid in place of an L-amino acid.

10. The isolated peptide of claim 1, wherein said peptide consists of SEQ ID NO: 1, 2, 3, or 4.

11. The isolated peptide of claim 1, wherein said peptide consists of SEQ ID NO: 4.

* * * * *

```
                           SEQUENCE LISTING

<160> NUMBER OF SEQ ID NOS: 29

<210> SEQ ID NO 1
<211> LENGTH: 58
<212> TYPE: PRT
<213> ORGANISM: Artificial Sequence
<220> FEATURE:
<223> OTHER INFORMATION: peptide from human Factor V

<400> SEQUENCE: 1

Ser Arg Ala Trp Gly Glu Ser Thr Pro Leu Ala Asn Lys Pro Gly Lys
  1               5                  10                  15

Gln Ser Gly His Pro Lys Phe Pro Arg Val Arg His Lys Ser Leu Gln
             20                  25                  30

Val Arg Gln Asp Gly Gly Lys Ser Arg Leu Lys Lys Ser Gln Phe Leu
         35                  40                  45

Ile Lys Thr Arg Lys Lys Lys Glu Lys
     50                  55

<210> SEQ ID NO 2
<211> LENGTH: 46
<212> TYPE: PRT
<213> ORGANISM: Artificial Sequence
<220> FEATURE:
<223> OTHER INFORMATION: peptide from human Factor V

<400> SEQUENCE: 2

Lys Pro Gly Lys Gln Ser Gly His Pro Lys Phe Pro Arg Val Arg His
  1               5                  10                  15

Lys Ser Leu Gln Val Arg Gln Asp Gly Gly Lys Ser Arg Leu Lys Lys
             20                  25                  30

Ser Gln Phe Leu Ile Lys Thr Arg Lys Lys Lys Glu Lys
         35                  40                  45

<210> SEQ ID NO 3
<211> LENGTH: 25
<212> TYPE: PRT
<213> ORGANISM: Artificial Sequence
<220> FEATURE:
<223> OTHER INFORMATION: peptide from human Factor V

<400> SEQUENCE: 3

Arg Gln Asp Gly Gly Lys Ser Arg Leu Lys Lys Ser Gln Phe Leu Ile
  1               5                  10                  15

Lys Thr Arg Lys Lys Lys Glu Lys
             20                  25

<210> SEQ ID NO 4
<211> LENGTH: 26
<212> TYPE: PRT
<213> ORGANISM: Artificial Sequence
<220> FEATURE:
<223> OTHER INFORMATION: peptide from human tissue factor pathway
      inhibitor

<400> SEQUENCE: 4

Lys Lys Gly Phe Ile Gln Arg Ile Ser Lys Gly Gly Leu Ile Lys Thr
  1               5                  10                  15
```

Lys Arg Lys Arg Lys Lys Gln Arg Val Lys
            20                  25

<210> SEQ ID NO 5
<211> LENGTH: 131
<212> TYPE: PRT
<213> ORGANISM: Homo sapiens

<400> SEQUENCE: 5

Leu Leu Leu Leu Lys Gln Ser Asn Ser Ser Lys Ile Leu Val Gly Arg
  1               5                  10                  15

Trp His Leu Ala Ser Glu Lys Gly Ser Tyr Glu Ile Ile Gln Asp Thr
            20                  25                  30

Asp Glu Asp Thr Ala Val Asn Asn Trp Leu Ile Ser Pro Gln Asn Ala
        35                  40                  45

Ser Arg Ala Trp Gly Glu Ser Thr Pro Leu Ala Asn Lys Pro Gly Lys
    50                  55                  60

Gln Ser Gly His Pro Lys Phe Pro Arg Val Arg His Lys Ser Leu Gln
65                  70                  75                  80

Val Arg Gln Asp Gly Gly Lys Ser Arg Leu Lys Lys Ser Gln Phe Leu
                85                  90                  95

Ile Lys Thr Arg Lys Lys Lys Glu Lys His Thr His His Ala Pro
            100                 105                 110

Leu Ser Pro Arg Thr Phe His Pro Leu Arg Ser Glu Ala Tyr Asn Thr
        115                 120                 125

Phe Ser Glu
    130

<210> SEQ ID NO 6
<211> LENGTH: 46
<212> TYPE: PRT
<213> ORGANISM: Homo sapiens

<400> SEQUENCE: 6

Lys Pro Gly Lys Gln Ser Gly His Pro Lys Phe Pro Arg Val Arg His
  1               5                  10                  15

Lys Ser Leu Gln Val Arg Gln Asp Gly Gly Lys Ser Arg Leu Lys Lys
            20                  25                  30

Ser Gln Phe Leu Ile Lys Thr Arg Lys Lys Lys Glu Lys
        35                  40                  45

<210> SEQ ID NO 7
<211> LENGTH: 46
<212> TYPE: PRT
<213> ORGANISM: Sus scrofa

<400> SEQUENCE: 7

Lys His Gly Lys Gln Arg Gly His Pro Ile Phe Val Thr Arg His Lys
  1               5                  10                  15

Leu Leu Gln Glu Arg Gln Asp Glu Gly Asn Ser Ile Leu Lys Lys Gly
            20                  25                  30

Arg Phe Phe Ile Arg Thr Arg Arg Lys Lys Lys Glu Arg Lys
        35                  40                  45

<210> SEQ ID NO 8
<211> LENGTH: 49
<212> TYPE: PRT
<213> ORGANISM: Bos taurus

<400> SEQUENCE: 8

Lys Asn Ser His Gly Lys Gln Ser Gly His Pro Thr Phe Leu Val Thr
1               5                   10                  15

Arg Arg Lys Pro Leu Gln Asp Arg Gln Asp Arg Arg Asn Ser Arg Leu
            20                  25                  30

Lys Glu Gly Leu Pro Leu Ile Arg Thr Arg Arg Lys Lys Lys Glu Glu
        35                  40                  45

Lys

<210> SEQ ID NO 9
<211> LENGTH: 45
<212> TYPE: PRT
<213> ORGANISM: Mus musculus

<400> SEQUENCE: 9

Arg Lys Pro Ser Asp Leu Pro Thr Phe Ser Gly Val Gly His Lys Ser
1               5                   10                  15

Pro His Val Arg Gln Glu Glu Glu Asn Ser Gly Phe Gln Lys Arg Gln
            20                  25                  30

Leu Phe Ile Arg Thr Arg Lys Lys Lys Asn Lys Lys
        35                  40                  45

<210> SEQ ID NO 10
<211> LENGTH: 53
<212> TYPE: PRT
<213> ORGANISM: Ornithorhynchus anatinus

<400> SEQUENCE: 10

Arg Gln Gly Arg Pro Val Ser His Gln Lys Phe Ala Glu His Arg Gln
1               5                   10                  15

Lys Ile Lys Arg Ala Arg Pro Lys Phe Leu Asn Gln Gly Ala Asp Gly
            20                  25                  30

Glu Ser Thr Pro Ile Arg Pro Ala Met Thr Phe Ile Lys Thr Arg Arg
        35                  40                  45

Lys Lys Ile Asp Lys
        50

<210> SEQ ID NO 11
<211> LENGTH: 56
<212> TYPE: PRT
<213> ORGANISM: Gallus gallus

<400> SEQUENCE: 11

Lys His His Lys Lys Asp Gly Glu Phe Ser His Leu Met Gly Glu
1               5                   10                  15

Lys His Lys Gly Asn His Met Arg Ser Pro Leu Lys Arg Lys Glu Gly
            20                  25                  30

Asn Lys Asn Asp Thr Leu Ser Ile Ser Gly Thr Phe Val Lys Ile Arg
        35                  40                  45

Arg Lys Lys Lys Glu Tyr Pro Lys
        50                  55

<210> SEQ ID NO 12
<211> LENGTH: 48
<212> TYPE: PRT
<213> ORGANISM: Anolis carolinensis

<400> SEQUENCE: 12

Lys Lys Asn Lys Lys Ala Tyr Lys Glu Asn Ser Leu Pro Glu Leu Gly

-continued

```
                1               5                   10                  15
            Gln Ala Glu Ile Asn Asn Lys Asn Lys Val Leu Asn Glu Gln Arg Tyr
                            20                  25                  30
            Glu Asn Ser Ser Ser Gly Thr Phe Ile Lys Ile Arg Arg Lys Glu Lys
                        35                  40                  45
```

<210> SEQ ID NO 13
<211> LENGTH: 39
<212> TYPE: PRT
<213> ORGANISM: Xenopus tropicalis

<400> SEQUENCE: 13

```
            Lys Thr Gln Glu Glu Gln Asn Ala Lys Lys Pro Thr Lys Arg Tyr Phe
             1               5                   10                  15
            Gln Val Arg Pro Ile Arg Tyr Arg Thr Ser Ser Asn Glu Thr Arg Met
                            20                  25                  30
            Leu Thr Arg Arg Lys Lys Arg
                        35
```

<210> SEQ ID NO 14
<211> LENGTH: 44
<212> TYPE: PRT
<213> ORGANISM: Danio rerio

<400> SEQUENCE: 14

```
            Lys Tyr Val Lys Asp Lys Ser Ala Ala Asn Ser Asn Lys Pro Lys Ile
             1               5                   10                  15
            Glu Lys Glu Lys Lys Val Tyr Gln Arg Val Lys Pro Lys Lys Gly
                            20                  25                  30
            Tyr Gly Met Lys Thr Lys Lys Ser Lys Asp Tyr Lys
                        35                  40
```

<210> SEQ ID NO 15
<211> LENGTH: 39
<212> TYPE: PRT
<213> ORGANISM: Takifugu rubripes

<400> SEQUENCE: 15

```
            Lys Lys Tyr Phe Glu Met Ser Pro Gln Thr Asn Lys Lys Lys Thr Arg
             1               5                   10                  15
            Lys Val Asn Arg Pro His Arg Pro Gln Lys Gly His Gly Met Lys Thr
                            20                  25                  30
            Lys Arg Arg Lys Glu Tyr Lys
                        35
```

<210> SEQ ID NO 16
<211> LENGTH: 47
<212> TYPE: PRT
<213> ORGANISM: Homo sapiens

<400> SEQUENCE: 16

```
            Thr Asp Tyr Ile Glu Ile Ile Pro Lys Glu Glu Val Gln Ser Ser Glu
             1               5                   10                  15
            Asp Asp Tyr Ala Glu Ile Asp Tyr Val Pro Tyr Asp Pro Tyr Lys
                            20                  25                  30
            Thr Asp Val Arg Thr Asn Ile Asn Ser Ser Arg Asp Pro Asp Asn
                        35                  40                  45
```

<210> SEQ ID NO 17
<211> LENGTH: 47

<212> TYPE: PRT
<213> ORGANISM: Sus scrofa

<400> SEQUENCE: 17

Gly Asp Tyr Val Glu Ile Ile Pro Arg Gln Gln Glu Asn Ser Glu
1               5                   10                  15

Glu Asp Tyr Val Lys Ile Asp Tyr Val Glu Tyr Asp Asp Pro Tyr Gln
                20                  25                  30

Thr Asp Val Arg Thr Asp Ile Asn Ser Ser Arg Asn Pro Asp Asn
            35                  40                  45

<210> SEQ ID NO 18
<211> LENGTH: 47
<212> TYPE: PRT
<213> ORGANISM: Bos taurus

<400> SEQUENCE: 18

Gly Asp Tyr Ile Glu Ile Ile Pro Arg Gln Lys Glu Ser Ser Glu
1               5                   10                  15

Glu Asp Tyr Gly Glu Phe Glu Phe Val Ala Tyr Asn Asp Pro Tyr Gln
                20                  25                  30

Thr Asp Leu Arg Thr Asp Ile Asn Ser Ser Arg Asn Pro Asp Asn
            35                  40                  45

<210> SEQ ID NO 19
<211> LENGTH: 47
<212> TYPE: PRT
<213> ORGANISM: Mus musculus

<400> SEQUENCE: 19

Gly Asp Asp Val Glu Ile Val Pro Ser Glu Glu Pro Glu Arg Ile Asp
1               5                   10                  15

Glu Asp Tyr Ala Glu Asp Asp Phe Val Thr Tyr Asn Asp Pro Tyr Arg
                20                  25                  30

Thr Asp Thr Arg Thr Asp Val Asn Ser Ser Arg Asn Pro Asp Thr
            35                  40                  45

<210> SEQ ID NO 20
<211> LENGTH: 47
<212> TYPE: PRT
<213> ORGANISM: Ornithorhynchus anatinus

<400> SEQUENCE: 20

Gly Asp Tyr Ile Glu Tyr Val Pro Gly Pro Glu Ile Gln Asn Ser Asp
1               5                   10                  15

Glu Asp Leu Ala Met Ile Gln Tyr Val Ala Tyr Asp Asn Pro Tyr Glu
                20                  25                  30

Asn Asp Phe Arg Ala Asn Pro Tyr Thr Leu Arg Asn Pro Asp Thr
            35                  40                  45

<210> SEQ ID NO 21
<211> LENGTH: 47
<212> TYPE: PRT
<213> ORGANISM: Gallus gallus

<400> SEQUENCE: 21

Gly Asn Tyr Glu Tyr Thr Ser Gly Glu Tyr Tyr Thr Glu Asp Thr Ser
1               5                   10                  15

Gly Asp Glu Tyr Glu Tyr Tyr Val Ser Phe Asp Asp Pro Tyr Met
                20                  25                  30

```
Thr Asp Pro Lys Leu Asn Val Asn Glu Gln Arg Asn Pro Asp Asp
            35                  40                  45
```

<210> SEQ ID NO 22
<211> LENGTH: 47
<212> TYPE: PRT
<213> ORGANISM: Anolis carolinensis

<400> SEQUENCE: 22

```
Asp Tyr Gln Glu Tyr Ile Ile Asp Asp Thr Asp Glu Asp Ser Thr
 1               5                  10                  15

Ser Asp Ser Phe Glu Tyr Gln Met Val His Tyr Asp Asn Pro Tyr Thr
                20                  25                  30

Met Asp Ser Arg Leu Asp Thr Ser Ala Ala Arg Asn Pro Asp Asn
            35                  40                  45
```

<210> SEQ ID NO 23
<211> LENGTH: 47
<212> TYPE: PRT
<213> ORGANISM: Xenopus tropicalis

<400> SEQUENCE: 23

```
Ile Ile Gly Leu Pro Gly Leu Asp Glu Gly Asp Tyr Val Glu Leu Asn
 1               5                  10                  15

Val Asp Glu Ile Asp Glu Asp Val His Ile Lys Lys Val Glu Tyr Glu
                20                  25                  30

Glu Leu Tyr Lys Thr Glu Ala Gln Gly Tyr Thr Asn Pro Asp Lys
            35                  40                  45
```

<210> SEQ ID NO 24
<211> LENGTH: 46
<212> TYPE: PRT
<213> ORGANISM: Danio rerio

<400> SEQUENCE: 24

```
Asn Asp Tyr Glu Leu Tyr Ile Pro Lys Gln Asp Gln Glu Ala Asp Phe
 1               5                  10                  15

Asp Gly Leu Leu Asp His Pro Glu Gly Tyr Glu Tyr Val Glu Tyr Lys
                20                  25                  30

Asp Pro Tyr Ser Lys Thr Ala Asp Val Gln Ala Leu Asp Ala
            35                  40                  45
```

<210> SEQ ID NO 25
<211> LENGTH: 47
<212> TYPE: PRT
<213> ORGANISM: Takifugu rubripes

<400> SEQUENCE: 25

```
Ser Asp Tyr Glu Leu Tyr Leu Pro Gly Asp Glu Pro Asp His Leu Asp
 1               5                  10                  15

Val Asp Gln Arg Asn Val Lys Ala Asn Glu Tyr Glu Tyr Val Asn Tyr
                20                  25                  30

Lys Asp Pro Tyr Arg Ser Asn Glu Asp Ala Lys Asn Leu His Leu
            35                  40                  45
```

<210> SEQ ID NO 26
<211> LENGTH: 39
<212> TYPE: DNA
<213> ORGANISM: Artificial Sequence
<220> FEATURE:
<223> OTHER INFORMATION: primer

```
<400> SEQUENCE: 26
gcaaggtctc aaggttcacg tgcttgggga gaaagcacc                           39

<210> SEQ ID NO 27
<211> LENGTH: 53
<212> TYPE: DNA
<213> ORGANISM: Artificial Sequence
<220> FEATURE:
<223> OTHER INFORMATION: primer

<400> SEQUENCE: 27
gcttgtcgac ttacttctct tttttctttt ttcgtgtctt aatgagaaac tgg          53

<210> SEQ ID NO 28
<211> LENGTH: 40
<212> TYPE: DNA
<213> ORGANISM: Artificial Sequence
<220> FEATURE:
<223> OTHER INFORMATION: primer

<400> SEQUENCE: 28
gcaaggtctc aaggtagtgg ccacccaaag tttcctagag                          40

<210> SEQ ID NO 29
<211> LENGTH: 48
<212> TYPE: DNA
<213> ORGANISM: Artificial Sequence
<220> FEATURE:
<223> OTHER INFORMATION: primer

<400> SEQUENCE: 29
gcttgtcgac ttagttgtca ggatctctgg aggagttgat gtttgtcc                 48
```